US008734853B2

(12) United States Patent
Sood et al.

(10) Patent No.: US 8,734,853 B2
(45) Date of Patent: May 27, 2014

(54) HDL PARTICLES FOR DELIVERY OF NUCLEIC ACIDS

(75) Inventors: Anil K. Sood, Pearland, TX (US); Andras G. Lacko, Ft. Worth, TX (US); Gabriel Lopez-Berestein, Bellaire, TX (US); Lingegowda S. Mangala, Webster, TX (US); Walter J. McConathy, Midland, TX (US); Laszlo Prokai, Mansfield, TX (US); Maya P. Nair, Coppell, TX (US)

(73) Assignees: University of North Texas Health Science Center at Fort Worth, Fort Worth, TX (US); The Board of Regents, The University of Texas System, Austin, TX (US)

( * ) Notice: Subject to any disclaimer, the term of this patent is extended or adjusted under 35 U.S.C. 154(b) by 307 days.

(21) Appl. No.: 13/129,349

(22) PCT Filed: Nov. 17, 2009

(86) PCT No.: PCT/US2009/064834
§ 371 (c)(1),
(2), (4) Date: Sep. 2, 2011

(87) PCT Pub. No.: WO2010/057203
PCT Pub. Date: May 20, 2010

(65) Prior Publication Data
US 2011/0312899 A1    Dec. 22, 2011

Related U.S. Application Data

(60) Provisional application No. 61/115,387, filed on Nov. 17, 2008.

(51) Int. Cl.
*A61K 9/14* (2006.01)
*A61K 31/7088* (2006.01)
*A61K 31/7105* (2006.01)

(52) U.S. Cl.
USPC .................. 424/499; 514/44 R; 514/44 A

(58) Field of Classification Search
None
See application file for complete search history.

(56) References Cited

U.S. PATENT DOCUMENTS

| 4,868,158 A | 9/1989 | Masquelier et al. ......... 514/19.3 |
| 5,128,318 A | 7/1992 | Levine et al. .................. 514/7.4 |

(Continued)

FOREIGN PATENT DOCUMENTS

| WO | WO 88/09345 | 12/1988 |
| WO | WO 98/13385 | 4/1998 |

(Continued)

OTHER PUBLICATIONS

Lewis et al. A walk through vertebrate and invertebrate protamines. Chromosoma. 2003, vol. 111, pp. 473-482.*

(Continued)

*Primary Examiner* — Jeffrey E Russel
(74) *Attorney, Agent, or Firm* — Parker Highlander PLLC

(57) ABSTRACT

Disclosed are high density lipoprotein-nucleic acid particles, wherein the particles include (a) an apolipoprotein; (b) a nucleic acid component comprising a therapeutic nucleic acid segment; and (c) a polypeptide comprising a positively charged region, wherein the positively-charged region of the polypeptide associates with the nucleic acid component. Also disclosed are pharmaceutical compositions that include a) an apolipoprotein; (b) a nucleic acid component comprising a therapeutic nucleic acid segment; and (c) a polypeptide comprising a positively charged region. Methods that concern the particles and pharmaceutical compositions of the present invention are also set forth, as well as kits.

25 Claims, 8 Drawing Sheets

(56) References Cited

U.S. PATENT DOCUMENTS

| | | | |
|---|---|---|---|
| 5,652,339 | A | 7/1997 | Lerch et al. .................. 530/359 |
| 5,874,059 | A | 2/1999 | Maranhao .................... 424/1.11 |
| 6,506,405 | B1 | 1/2003 | Desai et al. ................... 424/450 |
| 6,506,559 | B1 | 1/2003 | Fire et al. ..................... 435/6.16 |
| 6,514,523 | B1 | 2/2003 | Sparks .......................... 424/450 |
| 6,573,099 | B2 | 6/2003 | Graham ........................ 435/455 |
| 7,053,049 | B2 * | 5/2006 | Luescher et al. ............... 514/7.4 |
| 8,268,798 | B2 * | 9/2012 | Chatterton .................. 514/44 R |
| 2002/0156007 | A1 * | 10/2002 | Graversen et al. ............. 514/12 |
| 2002/0168707 | A1 | 11/2002 | Graham ....................... 435/69.1 |
| 2003/0008014 | A1 | 1/2003 | Shelness ....................... 424/499 |
| 2003/0051263 | A1 | 3/2003 | Fire et al. ........................ 800/13 |
| 2003/0055020 | A1 | 3/2003 | Fire et al. ..................... 514/44 A |
| 2003/0159161 | A1 | 8/2003 | Graham et al. ................... 800/8 |
| 2004/0064842 | A1 | 4/2004 | Graham et al. ................... 800/8 |
| 2004/0204354 | A1 | 10/2004 | Nelson et al. .................. 424/450 |
| 2004/0205839 | A1 | 10/2004 | Doutriaux et al. ............. 800/278 |
| 2004/0234588 | A1 | 11/2004 | Lu et al. ........................ 424/450 |
| 2004/0266662 | A1 | 12/2004 | Rye et al. ...................... 435/134 |
| 2008/0138394 | A1 | 6/2008 | Kim et al. ...................... 424/450 |
| 2008/0253960 | A1 | 10/2008 | Zheng et al. ................... 514/1.1 |
| 2009/0110739 | A1 | 4/2009 | Lacko et al. .................. 424/491 |

FOREIGN PATENT DOCUMENTS

| | | |
|---|---|---|
| WO | WO 98/46275 | 10/1998 |
| WO | WO 99/04761 | 2/1999 |
| WO | WO 01/13939 | 3/2001 |
| WO | WO 03/029294 | 4/2003 |
| WO | WO 2005/039534 | 5/2005 |
| WO | WO 2006/073419 | 7/2006 |
| WO | WO 2006/100567 | 9/2006 |
| WO | WO 2009/073984 | 6/2009 |

OTHER PUBLICATIONS

Adams, et al., "Safety and utilization of blood components as therapeutic delivery systems," *Curr. Pharm. Biotechnol.*, 4:275-82, 2003.

Ajees, et al., "Crystal structure of human apolipoprotein A-I: insights into its protective effect against cardiovascular diseases," *Proc. Natl. Acad. Sci. USA*, 103:2126-31, 2006.

Akhtar and Benter, "Nonviral delivery of synthetic siRNAs in vivo," *J. Clin. Invest.*, 117:3623-32, 2007.

Alexander, et al., "Apolipoprotein A-I helix 6 negatively charged residues attenuate lecithin-cholesterol acyltransferase (LCAT) reactivity," *Biochemistry*, 44:5409-19, 2005.

Anantharamaiah, et al., "Role of amphipathic helixes in HDL structure/function," *Adv. Exp. Med. Biol.*, 285:131-40, 1991.

Bijsterbosch, et al., "Native and modified lipoproteins as drug delivery systems," *Adv. Drug Deliv. Rev.*, 5:231-51, 1990.

Bijsterbosch, et al., "Specific targeting of a lipophilic prodrug of iododeoxyuridine to parenchymal liver cells using lactosylated reconstituted high density lipoprotein particles," *Biochem. Pharmacol.*, 52:113-21, 1996.

Bijsterbosch, et al., "Synthesis of the dioleoyl derivative of iododeoxyuridine and its incorporation into reconstituted high density lipoprotein particles," *Biochemistry*, 33:14073-80, 1994.

Calvo, et al., "Clinical proteomics: from biomarker discovery and cell signaling profiles to individualized personal therapy," *Bioscience Reports*, 25:107-25, 2005.

Chen, et al., "Ligand conjugated low-density lipoprotein nanoparticles for enhanced optical cancer imaging in vivo," *J. Am. Chem. Soc.*, 129:5798-9, 2007.

Clay, et al., "Formation of spherical, reconstituted high density lipoproteins containing both apolipoproteins A-I and A-II is mediated by lecithin:cholesterol acyltransferase," *J. Biol. Chem.*, 275:9019-25, 2000.

Constantinides, et al., "Tocol emulsions for drug solubilization and parenteral delivery," *Adv. Drug Deliv. Rev.*, 56:1243-55, 2004.

Corbin, et al., "Enhanced cancer-targeted delivery using engineered high density lipoprotein-based nanocarriers," *J. Biomed. Nanotechnol.*, 3:367-76, 2007.

Corbin and Zheng, "Mimicking nature's nanocarrier: synthetic low-density lipoprotein-like nanoparticles for cancer-drug delivery," *Nanomedicine*, 2:375-80, 2007.

Davis, "Coming of age of lipid-based drug delivery systems," *Adv. Drug Deliv. Rev.*, 56:1241-2, 2004.

de Paula, et al., "Hydrophobization and bioconjugation for enhanced siRNA delivery and targeting," *RNA*, 13:431-56, 2007.

de Vrueh, et al., "Carrier-mediated delivery of 9-(2-phosphonylmethoxyethyl)adenine to parenchymal liver cells: a novel therapeutic approach for hepatitis B," *Antimicrob. Agents Chemother.*, 44:477-83, 2000.

de Vrueh, et al., "Cryopreservation enables long-term storage of 9-(2-phosphonylmethoxyethyl)adenine prodrug-loaded reconstituted lactosylated high-density lipoprotein," *Pharm. Res.*, 18:403-7, 2001.

de Vrueh, et al., "Synthesis of a lipophilic prodrug of 9-(2-phosphonylmethoxyethyl)adenine (PMEA) and its incorporation into a hepatocyte-specific lipidic carrier," *Pharm. Res.*, 16:1179-85, 1999.

Edelstein, et al., "On the mechanism of the displacement of apolipoprotein A-I by apolipoprotein A-II from the high density lipoprotein surface. Effect of concentration and molecular forms of apolipoprotein A-II," *J. Biol. Chem.*, 257:7189-95, 1982.

Elmén, et al., "Locked nucleic acid (LNA) mediated improvements in siRNA stability and functionality," *Nucleic Acids Res.*, 33:439-47, 2005.

Favre, et al., "High density lipoprotein3 binding sites are related to DNA biosynthesis in the adenocarcinoma cell line A549," *J. Lipid Res.*, 34:1093-106, 1993.

Feng, et al., "Liver targeting and anti-HBV activity of reconstituted HDL-acyclovir palmitate complex," *Eur. J. Pharm. Biopharm.*, 68:688-93, 2008.

Feng, et al., "Recombinant high-density lipoprotein complex as a targeting system of nosiheptide to liver cells," *J. Drug Target*, 16:502-8, 2008.

Halder, et al., "Therapeutic efficacy of a novel focal adhesion kinase inhibitor TAE226 in ovarian carcinoma," *Cancer Research*, 67:10976-83, 2007.

International Search Report and Written Opinion, issued in PCT/US2009/064834, dated Jul. 22, 2010.

Jonas, "Lecithin-cholesterol acyltransferase in the metabolism of high-density lipoproteins," *Biochim. Biophys. Acta.*, 1084:205-20, 1991.

Kader and Pater, "Loading anticancer drugs into HDL as well as LDL has little affect on properties of complexes and enhances cytotoxicity to human carcinoma cells," *J. Control Release*, 80:29-44, 2002.

Kawakami and Hashida, "Targeted delivery systems of small interfering RNA by systemic administration," *Drug Metab. Pharmacokinet.*, 22:142-51, 2007.

Kim, et al., "Cationic solid lipid nanoparticles reconstituted from low density lipoprotein components for delivery of siRNA," *Mol. Pharm.*, 5:622-31, 2008.

Kim, et al., "Systemic and specific delivery of small interfering RNAs to the liver mediated by apolipoprotein A-1," *Molecular Therapy*, 15:1145-52, 2007.

Kirpotin, et al., "Antibody targeting of long-circulating lipidic nanoparticles does not increase tumor localization but does increase internalization in animal models," *Cancer Res.*, 66:6732-40, 2006.

Kratzer, et al., "Apolipoprotein A-I coating of protamine-oligonucleotide nanoparticles increases particle uptake and transcytosis in an in vitro model of the blood-brain barrier," *J. Control Release*, 117:301-11, 2007.

Kumar and Clarke, "Gene manipulation through the use of small interfering RNA (siRNA): from in vitro to in vivo applications," *Adv. Drug Deliv. Rev.*, 59:87-100, 2007.

Lacko, et al., "High density lipoprotein complexes as delivery vehicles for anticancer drugs," *Anticancer Res.*, 22:2045-9, 2002.

Lacko, et al., "Recent developments and patenting of lipoprotein based formulations," *Recent Pat. Drug Deliv. Formul.*, 1:143-5, 2007.

Landen, et al., "Efficacy and antivascular effects of EphA2 reduction with an agonistic antibody in ovarian cancer," *J. Natl. Cancer Inst.*, 98:1558-70, 2006.

(56) References Cited

OTHER PUBLICATIONS

Landen, et al., "Therapeutic EphA2 gene targeting in vivo using neutral liposomal small interfering RNA delivery," *Cancer Res.*, 65:6910-8, 2005.

Leung and Whittaker, "RNA interference: from gene silencing to gene-specific therapeutics," *Pharmacol. Ther.*, 107:222-39, 2005.

Lou, et al., "High-density lipoprotein as a potential carrier for delivery of a lipophilic antitumoral drug into hepatoma cells," *World J. Gastroenterol.*, 11:954-9, 2005.

Lukyanov and Torchilin, "Micelles from lipid derivatives of water-soluble polymers as delivery systems for poorly soluble drugs," *Adv. Drug Deliv. Rev.*, 56:1273-89, 2004.

Lundberg, "A submicron lipid emulsion coated with amphipathic polyethylene glycol for parenteral administration of paclitaxel (Taxol)," *J. Pharm. Pharmacol.*, 49:16-21, 1997.

Massey, et al., "Human plasma high density apolipoprotein A-I: effect of protein-protein interactions on the spontaneous formation of a lipid-protein recombinant," *Biochem. Biophys. Res. Commun.*, 99:466-74, 1981.

Matz and Jonas, "Micellar complexes of human apolipoprotein A-I with phosphatidylcholines and cholesterol prepared from cholate-lipid dispersions," *J. Biol. Chem.*, 257:4535-40, 1982.

McConathy, et al., "Evaluation of synthetic/reconstituted high-density lipoproteins as delivery vehicles for paclitaxel," *Anticancer Drugs*, 19:183-8, 2008.

McGuire and Ozols, "Chemotherapy of advanced ovarian cancer," *Semin. Oncol.*, 25:340-8, 1998.

Merritt, et al., "Dicer, Drosha, and outcomes in patients with ovarian cancer," *N. Engl. J. Med.*, 359:2641-50, 2008.

Navab, et al., "Apolipoprotein A-I mimetic peptides and their role in atherosclerosis prevention," *Nat. Clin. Pract. Cardiovasc. Med.*, 3:540-7, 2006.

Navab, et al., "Apolipoprotein A-I mimetic peptides," *Arterioscler. Thromb. Vasc. Biol.*, 25:1325-31, 2005.

Ng, et al., "Lipoprotein-inspired nanoparticles for cancer theranostics," *Accounts of Chemical Research*, 44:1105-13, 2011.

Nikanjam, et al., "Synthetic nano-low density lipoprotein as targeted drug delivery vehicle for glioblastoma multiforme," *Int. J. Pharm.*, 328:86-94, 2007.

Pan, et al., "In vitro gene transfection in human glioma cells using a novel and less cytotoxic artificial lipoprotein delivery system," *Pharm. Res.*, 20:738-44, 2003.

Pittman, et al., "Synthetic high density lipoprotein particles: application to studies of the apoprotein specificity for selective uptake of cholesterol esters," *J. Biol. Chem.*, 262:2435-42, 1987.

Powers, "DLVR hopes to 'deliver' on siRNA potential in cancer," *BioWorld Today*, 22:1-2, 2011.

Pownall, "Remodeling of human plasma lipoproteins by detergent perturbation," *Biochemistry*, 44:9714-22, 2005.

Rensen, et al., "Recombinant lipoproteins: lipoprotein-like lipid particles for drug targeting," *Adv. Drug Deliv. Rev.*, 47:251-76, 2001.

Ryan, et al., "Optimized bacterial expression of human apolipoprotein A-I," *Protein Expr. Purif.*, 27:98103, 2003.

Saito, et al., "Contributions of domain structure and lipid interaction to the functionality of exchangeable human apolipoproteins," *Prog. Lipid Res.*, 43:350-80, 2004.

Schouten, et al., "Development of lipoprotein-like lipid particles for drug targeting: neo-high density lipoproteins," *Mol. Pharmacol.*, 44:486-92, 1993.

Shahzad, et al., "Targeted delivery of small interfering RNA using reconstituted high-density lipoprotein nanoparticles[1,2]," *Neoplasia*, 13:309-19, 2011.

Sodhi and Gould, "Combination of delipidized high density lipoprotein with lipids," *J. Biol. Chem.*, 242:1205-10, 1967.

Soutschek, et al., "Therapeutic silencing of an endogenous gene by systemic administration of modified siRNAs," *Nature*, 432:173-8, 2004.

Thaker, et al., "Antivascular therapy for orthotopic human ovarian carcinoma through blockade of the vascular endothelial growth factor and epidermal growth factor receptors," *Clin. Cancer Res.*, 11:4923-33, 2005.

Vingerhoeds, et al., "Immunoliposome-mediated targeting of doxorubicin to human ovarian carcinoma in vitro and in vivo," *Br. J. Cancer*, 74:1023-9, 1996.

Wang, et al., "Preparation and characterization of poly(lactic-co-glycolic acid) microspheres for targeted delivery of a novel anticancer agent, taxol," *Chem. Pharm. Bull.* (Tokyo), 44:1935-40, 1996.

Wolfrum, et al., "Mechanism and optimization of in vivo delivery of lipophilic siRNAs," *Nature Biotechnology*, 25:1149-57, 2007.

Xie, et al., "Down-regulation of Bcl-XL by RNA interference suppresses cell growth and induces apoptosis in human esophageal cancer cells," *World J. Gastroenterol.*, 12:7472-7, 2006.

Yang, et al., "Attenuation of nontargeted cell-kill using a high-density lipoprotein-mimicking peptide—phospholipid nanoscaffold," *Nanomedicine* (Lond.), 6:631-41, 2011.

Yang, et al., "Efficient cytosolic delivery of siRNA using HDL-mimicking nanoparticles," *Small*, 7:568-73, 2011.

Zhang, et al., "Biomimetic nanocarrier for direct cytosolic drug delivery," *Angew. Chem. Int. Ed. Engl.*, 48:9171-5, 2009.

Zhang, et al., "HDL-mimicking peptide-lipid nanoparticles with improved tumor targeting," *Small*, 6:430-7, 2010.

Zheng, et al., "Rerouting lipoprotein nanoparticles to selected alternate receptors for the targeted delivery of cancer diagnostic and therapeutic agents," *Proc. Natl. Acad. Sci. USA*, 102:17757-62, 2005.

\* cited by examiner

Lys-Lys-Lys-Lys-Lys-Lys-Lys-Lys-Lys-Lys-Lys-Lys
C-C-A-C-C-T-G-G-G-C-C-A-G-T-A-T-T-A-T
G-G-T-G-G-A-C-C-C-G-G-T-C-A-T-A-A-T-A
Lys-Lys-Lys-Lys-Lys-Lys-Lys-Lys-Lys-Lys-Lys-Lys

SEQUENCE LISTING

```
<160> NUMBER OF SEQ ID NOS: 6

<210> SEQ ID NO 1
<211> LENGTH: 19
<212> TYPE: RNA
<213> ORGANISM: Artificial Sequence
<220> FEATURE:
<223> OTHER INFORMATION: Synthetic primer

<400> SEQUENCE: 1
gccucucugc agaauucaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Synthetic primer

<400> SEQUENCE: 2
ccaccugggc caguauuau                                                  19

<210> SEQ ID NO 3
<211> LENGTH: 19
<212> TYPE: RNA
<213> ORGANISM: Artificial Sequence
<220> FEATURE:
<223> OTHER INFORMATION: Synthetic primer

<400> SEQUENCE: 3
uucuccgaac gugucacgu                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
ggtggacccg gtcataata                                                  19

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
ccacctgggc cagtattat                                                  19

<210> SEQ ID NO 6
<211> LENGTH: 18
<212> TYPE: PRT
<213> ORGANISM: Artificial Sequence
<220> FEATURE:
<223> OTHER INFORMATION: Synthetic Peptide
```

```
<400> SEQUENCE: 6

Lys Lys Lys Lys Lys Lys Lys Lys Lys Lys Lys Lys Lys Lys Lys
1               5                   10                  15
Lys Lys
```

HDL PARTICLES FOR DELIVERY OF NUCLEIC ACIDS

The present application is a national phase application under 35 U.S.C. §371 of International Application No. PCT/US2009/064834 filed Nov. 17, 2009 which claims the benefit of the filing date of U.S. Provisional Patent Application Ser. No. 61/115,387, filed Nov. 17, 2008, the contents of which is herein incorporated by reference in its entirety.

BACKGROUND OF THE INVENTION

1. Field of the Invention

The present invention relates generally to the fields of drug delivery, molecular biology and therapeutics. More particularly, it concerns high density lipoprotein (HDL) particles for the delivery of nucleic acids into cells and tissues, and compositions, methods, and kits that involve the HDL particles.

2. Description of Related Art

The therapeutic effectiveness of nucleic acids, such as genes, gene fragments, antisense nucleic acids, and interference RNA molecules has long been hampered by relatively inefficient delivery systems for these molecules into specific cells and tissues. To date, for example, the utility of small interference RNA (siRNA) as a therapeutic modality has been hampered by limitations posed by the negatively-charged siRNA that is unable to penetrate the negatively-charged cell membranes. These limitations have been discussed in numerous review articles (see, e.g., Kawakami and Hashida, 2007; Kumar and Clarke, 2007; Xie et al., 2006; Akhtar and Benter, 2007; and De Paula et al., 2007).

Macromolecular complexes containing lipids (liposomes) have been utilized as delivery vehicles for therapeutic agents, such as proteins, interleukins, cancer chemotherapeutic agents and antisense oligonucleotides (see, e.g., Chonn and Cullis, 1995; Wang et al., 1996; Lundberg, 1997; Weiner, 1994; Bergers et al., 1993; Tani et al., 1994). Other approaches to attempt to improve delivery of therapeutic agents include incorporation of specialized lipids or polyethylene glycol into liposomes for extending the residence time of the particles in the circulation (Wang et al., 1996; Allen, 1994) and the attachment of targeting signals such as glycolipids, proteins, antigens or antibodies to the liposome complex (Vingerhoeds et al., 1996). Despite these improvements and advances, toxic side effects remain a serious concern (McGuire and Ozols, 1998; Fanning et al., 1993; McGuire et al., 1996; Feenstra et al., 1997).

Regarding high density lipoproteins (HDLs), while preparations of reconstituted HDL were described in 1967 (Sodhi and Gould, 1967),), they have been used primarily to characterize the physical and chemical properties of high density lipoproteins (Massey et al., 1981; Edelstein et al., 1982; Anantharamaiah et al., 1991) and to conduct HDL metabolism studies they have been used primarily to characterize the physical and chemical properties of high density lipoproteins (Massey et al., 1981; Edelstein et al., 1982; Anantharamaiah et al., 1991) and to conduct HDL metabolism studies (Eisenberg, 1984; Jonas, 1991) rather than focusing on therapeutic applications. A trial aimed at a clinical application involving lactosylated HDL to delivery antiviral drugs to liver tissue has been reported (Favre et al., 1993). Use of high density lipoprotein complexes as delivery for particular chemotherapeutic agents has been described (Lacko et al., 2002, Lacko et al, 2007, McConathy et al 2008).

Despite these and other related efforts, there is a continued need in the medical arts for more efficient techniques for the delivery of therapeutic agents, particularly nucleic acids.

SUMMARY OF THE INVENTION

The present invention is in part based on the finding that high density lipoprotein (HDL) particles can be employed for efficient delivery of nucleic acids to cells and tissues. The use of HDL over liposomes and other artificial complexes as transport vehicles is advantageous because they are smaller in size and their contents are rapidly internalized by receptors of specific cells, including receptors on the surface of tumor tissue. An additional advantage of HDL as a delivery vehicle for nucleic acids lies in the fact that the uptake of HDL core components by cells is facilitated by specific cell surface receptors. The HDL nanoparticles of the present invention include a positively charged polyamino acid, which neutralizes the negatively charged nucleic acid, thus allowing for successful incorporation of the nucleic acid into an HDL particle. The HDL drug delivery overcomes many of the previous barriers faced by nucleic acid therapy. Thus, the HDL particles of the present invention represent a new generation of drug carriers that are composed of natural ingredients and offer unlimited application for delivery of nucleic acids into cells and tissues.

Using one aspect of the technique of the present invention, the inventors have described a method of in vivo delivery for siRNA using reconstituted HDL (rHDL) nanoparticles into cells and tissues, and have demonstrated the successful delivery of fluorescently labeled siRNA into tumor tissue, liver, kidney, spleen, and lung of nude mice by intravenous injection, and the silencing of focal adhesion kinase (FAK) in vivo using targeted siRNA/rHDL nanoparticles. The approach of the present invention aids in overcoming the barriers of instability, non-specific immune responses, lack of targeting and rapid systemic elimination by encapsulation of the nucleic acid molecule in the HDL particle that in addition to protecting their therapeutic cargo are also able to provide targeting to tumor and other specific tissues. Because of the unlimited potential of the HDL nanoparticles toward tissue and tumor targets, the approach of the present invention has broad applications.

Particular aspects of the present invention concern particles that include an apolipoprotein and a nucleic acid component (a therapeutic nucleic acid segment, and a polypeptide comprising a positively-charged region), wherein the positively-charged region is associated with the nucleic acid component. The apolipoprotein can be any apolipoprotein, such as apolipoprotein A-I (Apo A-I), apolipoprotein A-II (Apo A-II), apolipoprotein A-IV (apo-A-IV), apolipoprotein A-V (apo-V), apolipoprotein B48 (Apo B48), apolipoprotein B100 (Apo B100), apolipoprotein C-I (Apo C-I), apolipoprotein C-II (Apo C-II), apolipoprotein C-III (Apo C-III), apolipoprotein C-IV, and apolipoprotein D (apoD). In specific embodiments, the apolipoprotein is Apo A-I.

In some embodiments, the particle is comprised of reconstituted high density lipoproteins. "Reconstituted high density lipoproteins" as used herein refer to spherical macromolecular complexes that contain at least three of the lipid and one protein component of the natural circulating HDL. Non-limiting examples of lipid components of natural circulating HDL include phosphatidyl choline, cholesterol, and cholesteryl ester.

A "polypeptide" as used herein refers to a consecutive series of two or more amino acid residues. The polypeptide may have a length of 2 to 2000 consecutive amino acids, 2 to 1000 consecutive amino acids, 2 to 500 consecutive amino acids, 2 to 400 consecutive amino acids, 2 to 300 consecutive amino acids, 2 to 200 consecutive amino acids, 2 to 100 consecutive amino acids, 2 to 50 consecutive amino acids, 2 to 40 consecutive amino acids, 2 to 30 consecutive amino acids, 2 to 20 consecutive amino acids, or 2 to 15 consecutive amino acids.

A positively charged region of a polypeptide is a region that includes a net positive charge, that includes at least one positively charged amino acid. In particular embodiments, the polypeptide includes two or more consecutive positively charged amino acid residues. The positively charged region has a net positive charge, and functions to neutralize the negatively charged nucleic acid molecule, which thus facilitates packaging of the nucleic acid molecule into HDL particles. For example, the positively charged amino acids may be lysine residues, histidine residues, arginine residues, positively charged non-natural amino acids, such as those described in U.S. Pat. No. 6,783,946, or a mixture of any of these residues. The amino acid segments can include any number of consecutive positively charged residues, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200 or more residues, or any range of residues derivable therein. In some embodiments, for example, the amino acid segment includes 2 to 40 consecutive lysine residues. In more particular embodiments, the amino acid segment comprises 2 to 40 consecutive lysine residues. In further embodiments, the amino acid segment comprises 2 to 20 consecutive lysine residues. In other embodiments, the amino acid segment comprises 2 to 15 consecutive lysine residues.

In some embodiments, the rHDL-nucleic acid particle of the present invention further includes a lipid component. For example, the lipid component may include a neutral phospholipid. Non-limiting examples of neutral phospholipids include phosphatidylcholine, phosphatidylethanolamine, 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), and lysophosphatidylethanolamine.

In particular embodiments, the lipid component includes cholesterol. In more particular embodiments, the lipid component includes a combination of cholesterol and cholesterol oleate.

The HDL-nucleic acid particle can be of any size, but in particular embodiments the particle has a molecular size of from about 100 Angstroms to about 500 Angstroms. In more particular embodiments, the particle has a molecular size of from about 100 Angstroms to about 300 Angstroms. The size may be dependent on the size of the nucleic acid component incorporated into the particle.

The HDL-nucleic acid particle can have a broad range in molecular weight. The weight is dependent on the size of the nucleic acid incorporated into the particle. For example, in some embodiments, the particle has a molecular weight of between about 100,000 Daltons to about 1,000,000 Daltons. In more particular embodiments, the particle has a molecular weight of between about 100,000 Daltons to about 500,000 Daltons. In specific embodiments, the particle has a molecular weight of between about 100,000 Daltons to about 300,000 Daltons.

The nucleic acid component may include any type of therapeutic nucleic acid. For example, the therapeutic nucleic acid may be nucleic acid that encodes a therapeutic agent, such as a protein. The therapeutic nucleic acid may inhibit the expression of a gene. The nucleic acid component may be a DNA or a RNA. The nucleic acid component may be an oligonucleotide of between about 2 to about 100 nucleobases in length, or it may be a polynucleotide of greater than 100 nucleobases in length. In specific embodiments, the nucleic acid component includes an interference RNA. For example, the interference RNA may be a siRNA, or a nucleic acid encoding a siRNA. For example, the siRNA may be a double-stranded nucleic acid of about 18 to about 100 nucleobases in length. In specific embodiments, the siRNA is 18 to 30 nucleobases in length. In certain embodiments, the nucleic acid component includes a shRNA or a nucleic acid encoding a shRNA. In some embodiments, the nucleic acid component comprises a siRNA that downregulates focal adhesion kinase (FAK) expression. In other embodiments, the nucleic acid component comprises a siRNA that downregulates STAT3 expression.

In some embodiments, the HDL-nucleic acid particle further includes one or more attached ligands to target the particle to a particular cell type or tissue type in a subject. The targeting ligand can be attached to the particle using any method known to those of ordinary skill in the art. In specific embodiments, the targeting ligand is attached to the protein component of the apolipoprotein by a covalent bond. Non-limiting types of targeting ligands include a small molecule, a peptide, a polypeptide, a protein, an antibody, or an antibody fragment. In some embodiments, the targeting ligand targets the particle to a tumor cell.

Further variation in compositional properties of the lipids can readily be achieved by introducing phosphoglycerides with a desired composition or employing other lipids (e.g., sphingomyelin, cationic lipids) when preparing the HDL-lipid mix. Alteration of surface properties by chemical modification of lipids or apolipoproteins may also be used to alter the specificity of tissue delivery and to enhance the effectiveness of therapies designed for targeting specific metastatic tumors. Because circulating HDL contains apolipoproteins (A-II, A-IV, C-I, C-II, E and F), other than apo-AI, addition of these alone or in combination may be used to enhance specificity of delivery to certain types of metastatic tumors. Peptide analogs of these apolipoproteins may also be employed in the design of specific HDL preparations as described for apo-A1.

The HDL-nucleic acid particles of the present invention may include a single therapeutic nucleic acid, or more than one therapeutic nucleic acid. The particles of the present invention may further include one or more additional therapeutic agents incorporated into the particle, which may or may not be nucleic acids. For example, the additional therapeutic agent may be a small molecule, a peptide, a polypeptide, a protein, an antibody, an antibody fragment, and so forth.

Also disclosed are pharmaceutical compositions that include any of the aforementioned HDL-nucleic acid particles and one or more pharmaceutically acceptable carriers. The carrier can be any pharmaceutically acceptable carrier. In specific embodiments, the carrier is an aqueous carrier. Non-limiting examples of aqueous carriers include water and saline.

Pharmaceutical compositions may include an apolipoprotein, a nucleic acid component comprising a therapeutic nucleic acid segment, and a polypeptide that includes a positively-charged region, wherein the positively-charged region is associated with the nucleic acid component, are also contemplated by the present invention.

The pharmaceutical compositions set forth herein may further include one or more therapeutic agents. The therapeutic agent may be any therapeutic agent known to those of ordinary skill in the art, such as a small molecule, a peptide, a polypeptide, a protein, an antibody, an antibody fragment, an oligonucleotide, a RNA, a DNA, a siRNA, a shRNA, and so forth. In particular embodiments, the composition of the present invention includes one or more chemotherapeutic agents. Non-limiting examples of chemotherapeutic agents are set forth in the specification below.

Also disclosed are methods of treating a subject with a disease that involves administering to the subject a pharmaceutically effective amount of any of the aforementioned compositions that include a HDL-nucleic acid particle of the present invention. In subject can be any subject, such as a mouse, a rat, a rabbit, a cat, a dog, a cow, a horse, a sheep, a goat, a primate, or a human. In specific embodiments, the subject is a human, such as a human in need of a therapeutic nucleic acid.

The disease to be treated can be any disease known to those of ordinary skill in the art which may be amenable to treatment with a therapeutic nucleic acid. For example, the disease may be a hyperproliferative disease, an infectious disease, an inflammatory disease, a degenerative disease, or an immune disease. In particular embodiments, the hyperproliferative disease is a disease associated with neovascularization. In more particular embodiments, the hyperproliferative disease is cancer. The cancer can be any type of cancer. For example, the cancer may be breast cancer, lung cancer, prostate cancer, ovarian cancer, brain cancer, liver cancer, cervical cancer, pancreatic cancer, colon cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia.

Some aspects of the methods set forth herein further involve identifying a subject in need of treatment. Identifying a subject in need of treatment can be by any method known to those of ordinary skill in the art. For example, identifying can be by physical examination, by diagnostic examination (such as through use of an imaging modality such as CT, MRI, SPECT, PET), and so forth.

The methods set forth herein may further involve the administration of one or more additional therapies to the subject. The type of therapy is largely dependent on the type of disease which is being treated. For example, where the disease is cancer, the additional therapy may be an anticancer therapy, such as a chemotherapeutic agent, radiation therapy, surgical therapy, immunotherapy, gene therapy, or a combination of these therapies. Non-limiting examples of chemotherapeutic agents include docetaxel, paclitaxel, chlorambucil, gencitabine, 6-thioguanine, mercaptupurine, methotrexate, cisplatin, oxaliplatin, carboplatin, vinbastine, etoposide, vincristine, daunomycin, capecitabine, procarbazine, mechlorethamine, cyclophosphamide, camptothecin, bleomycin, busulfan, dactinomycin, tamoxifen, raloxifene, and 5-fluorouracil.

The pharmaceutical compositions can be administered using any method known to those of ordinary skill in the art. For example, the composition may be administered to the subject intravenously, topically, locally, systemically, intraperitoneally, intratracheally, intratumorally, intramuscularly, endoscopically, intralesionally, percutaneously, subcutaneously, regionally, or by direct injection or perfusion. In specific embodiments, the composition is administered intravenously.

The present invention also concerns methods of delivering a nucleic acid segment into a cell that involves contacting the cell with an effective amount of a high density lipoprotein-nucleic acid particle of the present invention, wherein the nucleic acid segment is delivered into the cell. The cell can be any type of cell. In particular embodiments, the cell is a mammalian cell. In more particular embodiments, the cell is a tumor cell. In particular embodiments, the cell is a cell that expresses a receptor that binds to an apolipoprotein. In a specific embodiments, the cell expresses the SR-B1 receptor (Connelly et al, 2004).

Also disclosed are methods of improving the therapeutic efficacy of a chemotherapeutic agent in a subject with cancer, administering to a subject with cancer a pharmaceutically effective amount of a composition of the present invention, and administering a chemotherapeutic agent to the subject, wherein efficacy of the chemotherapeutic agent is improved. Efficacy may be improved relative to a reference level of efficacy, such as efficacy with chemotherapeutic agent alone. In some embodiments, the cancer is ovarian cancer or colon cancer. In particular embodiments, the drug is a taxane, such as paclitaxel or docetaxel.

Methods of reducing the risk of metastasis in a subject with cancer that involves administration to a subject with cancer a pharmaceutically effective amount of a pharmaceutical composition of the present invention area also set forth.

Also disclosed are methods of preparing a high density lipoprotein-nucleic acid particle that involve preparing a composition which includes: (i) a polypeptide that includes a positively charged region; and (ii) a nucleic acid component that includes a therapeutic nucleic acid segment; and combining the foregoing composition with an apolipoprotein, wherein a high density lipoprotein-nucleic acid particle is formed. As discussed above, the positively-charged region of the polypeptide functions to neutralize the negatively charged nucleic acid segment. In some embodiments, the method further involves including a neutral phospholipid in the composition that includes the polypeptide and the nucleic acid component. The neutral phospholipid may be any type of neutral phospholipid, including any of those which have been previously mentioned. In specific embodiments, the neutral phospholipid is phosphatidyl choline. In a specific embodiment, the composition that includes the polypeptide and the nucleic acid segment further includes phosphatidyl choline, cholesterol, and cholesteryl oleate.

The present invention also concerns kits which include a first sealed container that includes an apolipoprotein and a polypeptide comprising a positively-charged region as set forth above. The apolipoprotein and polypeptide can be any of those which have been discussed in the foregoing sections. In some embodiments, the first sealed container further includes a nucleic acid component that includes a therapeutic nucleic acid segment. In some embodiments, the first sealed container includes any of the aforementioned HDL-nucleic acid particles of the present invention. In other embodiments, the nucleic acid component is included in a second sealed container rather than the first sealed container. The nucleic acid component may be any of the aforementioned nucleic acid components. In specific embodiments, the nucleic acid component is a siRNA.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

FIG. 2. Proposed structure of the neutralized oligolysine/FAK-siRNA, appropriate for packaging into rHDL. Shown is a DNA sequence encoding the FAK-siRNA. The FAK-siRNA sequence is SEQ ID NO:2, and the DNA sequence encoding said sequence is SEQ ID NO:4 and its complement is SEQ ID NO:5. Also shown is a poly-lysine sequence (SEQ ID NO:6).

FIG. 3. Schematic structure of double-stranded FAK-siRNA, illustrating the highly negatively charged nature of the molecule. Shown is a DNA sequence encoding the FAK-siRNA. The FAK-siRNA sequence is SEQ ID NO:2, and the DNA sequence encoding said sequence is SEQ ID NO:4 and its complement is SEQ ID NO:5.

DESCRIPTION OF ILLUSTRATIVE EMBODIMENTS

Figure 1:
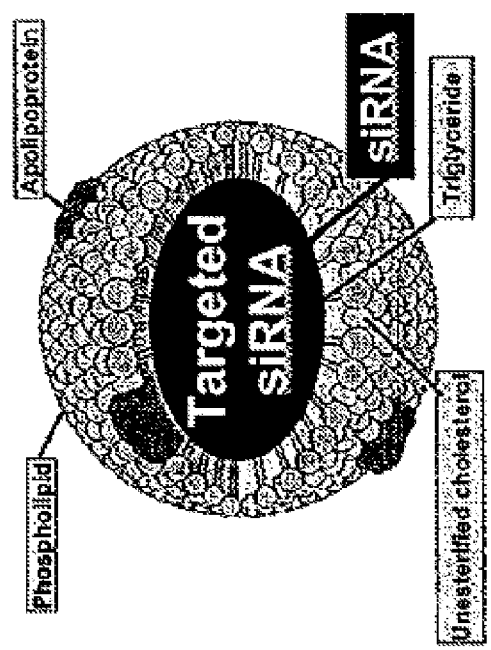
FIG. 1. Schematic depiction of the rHDL/siRNA complex (MW: est ~180,000).

To date, the utility of nucleic acids as a therapeutic modality has been limited by successful deliver the nucleic acid in vivo. The negatively-charged nucleic acid is often not taken up by negatively-charged cell membranes. The present invention in part concerns a method of in vivo delivery of nucleic acids using HDL-containing particles that allows highly reliable nucleic acid uptake by cells. The present inventors have demonstrated successful delivery of fluorescently-labeled siRNA into tumor, liver, kidney, spleen, and lung of nude mice by intravenous injection. Moreover, focal adhesion kinase (FAK) has been silenced in vivo using FAK targeted siRNA/rHDL nanoparticles. The approach of the present invention aids in overcoming many of the current barriers of nucleic acid delivery including instability, no-specific immune response, lack of targeting and rapid systemic elimination. Inclusion of the nucleic acid molecule in the rHDL nanoparticle protects the therapeutic cargo, and provides the option of targeting to tumor or other specific tissues.

A. Hdl-Nucleic Acid Particles

The invention provides compositions and methods for delivery of nucleic acids to cells and tissues, such as to individuals in need of a therapeutic nucleic acid. Delivery vehicles are provided in a formulation of a nucleic acid component that is encapsulated in a synthetic self-assembled particle. The interior of the particle represents a hydrophobic core region where nucleic acid neutralized by positively-charged amino acid residues of a polyeptide, such as lysine residues. In contrast to liposomes, which include an aqueous interior core surrounded by phospholipid bilayer, the nucleic acid carrier particles described herein are composed of a monolayer and a hydrophobic interior.

The hydrophobic nature of the interior of the HDL particles of the invention allows the encapsulation of nucleic acid, in a manner similar to the native core component of HDL (cholesteryl esters).

In one aspect, the invention provides a synthetic self-assembled "nanoparticle" (also termed "delivery particle" or rHDL/drug complex) that includes a lipid monolayer comprising a phosphatidylcholine (or similar amphipathic lipid), and a nucleic acid component. In some embodiments, a delivery particle may include one or more types of sphingomyelin or ether phospholipids.

"Self assembly (self assembled or self assembling)" in the case of the generation of rHDL nanoparticles means that the ingredients (such as lipids and proteins) or relatively low molecular weight (such as apo A-I with the molecular weight of 28,000) assembled into a particle of larger molecular weight (such as average molecular weight of about 180,000 or larger) without the application of a physical force, such as sonication, high pressure, membrane intrusion, or centrifugation. The advantages of self assembly from the standpoint of cancer chemotherapy are at least twofold: (1) the pharmaceutical agent incorporated into the self-assembled (McConathy et al 2008) versus the sonicated particle favors the former by over 20 fold (see, Lacko et al., 2002, McConathy et al., 2008). This increase of incorporation is a substantial advantage because of the substantially increased effective cytotoxicity of the self assembled particles toward cancer cells and tumors, and the increased uniformity of the self assembled particles compared to. those generated by physical force. This uniformity is also advantageous from the standpoint of more efficient delivery of the therapeutic nucleic acid to cells and tissue.

The interior of a particle includes a hydrophobic core region where the transported nucleic acid resides in a manner similar to the native cholesteryl esters in HDL. The particles are generally of spherical shape. Because of the natural components of the delivery particle, the complex formed by the encapsulation of the pharmaceutical agent is substantially non-immunogenic when administered to a subject.

1. Lipid Monolayer

The delivery particles of the invention may include a lipid monolayer with the polar head groups of phospholipids facing away from the interior of the particle, and a hydrophobic core region where the nucleic acid is encapsulated.

Any monolayer-forming lipid may be used that along with a lipid binding protein forms the scaffolding for the spherical particle to accommodate the nucleic acid. The term "monolayer-forming lipid" refers to a compound that is capable of forming a lipid monolayer serving as an outer shell of the basic lipoprotein structure. In some embodiments, the lipid monolayer is made up of phosphatidylcholine. Non-limiting examples of this include but are not limited to dimyristoyl PC (DMPC), dioleoyl-PC (DOPC), dipalmitoylphosphatidylcholine (DPPC), or other phospholipids such as, egg yolk phosphatidylcholine (egg PC), and soy bean phosphatidylcholine. In another embodiment sphingomyelin, cationic phospholipids or glycolipids may be used to form the monolayer to produce delivery particles with additional properties Particles able to perform controlled release of the encapsulated pharmaceutical could be prepared using these latter ingredients.

Neutral lipids may be incorporated into the HDL-nucleic acid particles of the present invention. "Neutral lipids" or "non-charged lipids," as used herein, are defined lipids (e.g., cholesterol, cholesterol ester, triglycerides) that yield an essentially-neutral, net charge (substantially non-charged). In certain embodiments of the present invention, a composition may be prepared wherein the lipid component of the composition is essentially neutral but is not in the form of liposomes.

Lipid compositions of the present invention may comprise phospholipids. In certain embodiments, a single kind or type of phospholipid may be used in the creation of lipid compositions such as liposomes (e.g., DOPC used to generate neutral liposomes). In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidyletanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidyletanolamine ("DMPE"), dipalmitoyl phosphatidyletanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidyletanolamine ("DOPE"), palmitoyloeoyl phosphatidylcholine ("POPC"), palmitoyloeoyl phosphatidyletanolamine ("POPE"), lysophosphatidylcholine, lysophosphatidyletanolamine, and dilinoleoylphosphatidylcholine.

Phospholipids include, for example, phosphatidylcholines, phosphatidylglycerols, and phosphatidyletanolamines; because phosphatidyletanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidyletanolamine are not used in certain embodiments as the primary phosphatide (i.e., constituting 50% or more of the total phosphatide composition) because this may result in instability and leakiness of the resulting liposomes.

2. Lipid Binding Proteins and Apolipoproteins

The term "lipid binding protein," as used here, refers to synthetic or naturally occurring peptides or proteins that are able to sustain a stable complex with lipid surfaces and thus able to function to stabilize the lipid monolayer of the nanoparticle of the invention. The HDL particles of the present invention may include one or more types of lipid binding proteins or apolipoproteins that are natural components of plasma lipoproteins (Ajees et al., 2006). In some embodiments, nanoparticles can be prepared using small synthetic peptides that may serve as surrogates for apo A-I (Navab et al., 2005) and thus yield formulations with additional properties once incorporated into the HDL particles of the present invention.

Two sources of HDL are available in bulk quantities as HDL apolipoproteins, including apoA-I. Bulk quantities of HDL may be prepared from salvage plasma or from blood product supernatants (such as a by-product of the cryopreipitation scheme at blood banks), according to Lacko and Chen, 1977. This method allows the isolation of HDL from plasma in excellent yield, and may be scaled to industrial production levels for production of apoA-I or other apoliripoproteins found in HDL. The HDL preparations can be subjected to Heparin-Sepharose chromatography to remove the apoE-containing fraction. The removal of apoE should enhance the specific uptake of the drug-HDL complexes by tumor cells vs non-malignant cells. The second source is the procurement of Cohn fraction IV, a by-product of albumin preparation and other serum proteins

3. Modified Lipid Binding Proteins

Apolipoproteins generally include a high content of amphipathic motif that facilitates their ability to bind to hydrophobic surfaces, including lipids. An important characteristic of apolipoptoteins is to support the structure of monolayers, vesicles or bilayers, composed primarily of phospholipids and to transform them into disc-shaped complexes (Saito et al., 2004). Subsequently, under physiological conditions, the discoidal complexes undergo a transition to a spherical structure (Alexander et al., 2005), facilitated by the enzyme lecithin cholesterol acyltransfetase (LCAT) to produce HDL.

The HDL-nucleic acid particles of the present invention may contain one or more pharmaceutical agents. The term "pharmaceutical agent" or "drug" as used herein refers to any compound or composition having preventive, therapeutic or diagnostic activity, primarily but not exclusively in the treatment of cancer patients.

In some embodiments, the lipid binding peptide or protein can be a synthetic analog or surrogate (Navab et al., 2006) for the naturally occurring apolipoprotein that is used in the preparation of the carrier particles.

4. Modified Lipid Binding Polypeptides

In some embodiments of the invention, a lipid binding protein (apo A-I) is used following chemical modification so that when the modified apo A-I is used as a component of the drug carrying delivery particle, it will have increased targeting ability. In one example, the apo A-I protein is modified by the attachment of folic acid residues that results in the doubling of the drug uptake by ovarian cancer cells compared to the non-modified formulation.

5. Delivery System for Delivery of a Nucleic Acid to an Individual

This approach provides a system comprised of delivery particles as a pharmaceutically acceptable formulation for delivering a nucleic acid. In some embodiments, the delivery system comprises an effective therapeutic approach to kill cancer cells or to destroy malignant tumors.

The term "effective amount" as used herein refers to the amount of a pharmaceutical sufficient to bring about the desired results in an experimental setting. A "therapeutically effective amount" or "therapeutic dose" refers to an amount of a pharmaceutical that is sufficient to produce beneficial clinical results, such as reduction in tumor size or remission for cancer patients.

The term "nanoparticle" as used herein refers to a particle with a diameter of less than about 1000 nm.

6. Targeting

The delivery particle of the invention may include a targeting ligand bound to the lipid binding protein component. For example, Apo A-I is the natural ligand for the HDL receptors. This receptor system allows the selective uptake of the natural core component, cholesteryl ester from HDL. Studies have demonstrated that the drug paclitaxel is also taken up by cancer cells via this receptor mediated mechanism, when encapsulated by HDL delivery particles (Lacko et al., 2002).

In some embodiments involving the treatment of malignant tissues, targeting is a major advantage because most cancerous growths have been shown to have enhanced receptor expression and thus would favor the uptake of the drug that is encased in the delivery particles compared to normal tissues and thus would reduce the danger of side effects.

In other embodiments, additional receptor binding components may be attached to a lipid binding protein component to enhance the targeting potential of the delivery vehicle. In one embodiment, folate is attached to the lipid binding protein. Folate receptors are upregulated in most ovarian tumors. Because nearly all cancer cells feature substantially higher expression of one or more specific surface antigens, ultimately individual therapy of patients will be possible following a proteomic screen of the tumor (Calvo et al., 2005). In another embodiment, the lipid binding protein moiety of the delivery particle may be modified to produce specifically targeted therapeutic strategies

7. Additional Therapeutic Agents

The particles of the present invention may optionally include one or more additional therapeutic agents. For example, the therapeutic agent may be a chemotherapeutic agent. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone;

podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

8. Production of HDL-Nucleic Acid Particles

The HDL-nucleic acid particles of the present invention can be made by different methods. For example, a nucleic acid (e.g., siRNA) may be neutralized by combining the nucleic acid with peptides or polypeptides composed of contiguous positively-charged amino acids. For example, as discussed above, amino acid sequences may include 2 or more contigous lysine residues. The positive charge of the amino acid sequences neutralizes the negatively charged nucleic acid molecule. The nucleic acid can then be encapsulated in an HDL particle using a method as described in Lacko et al. (2002).

In other embodiments, the neutralized nucleic acid sequence can be combined with apolipoprotein to form HDL-nucleic acid nanoparticles of the present invention. In particular embodiments, the neutralized nucleic acid sequence is combined with a mixture of phosphatidyl choline, cholesterol, and cholesteryl oleate, as set forth in the Example section below.

In another method, a mixture of lipids (cholesterol (C)/cholesteryl oleate (CE/egg yolk phosphatidyl choline (PC), molar ratio of 1:5:1.3:115) is dried under a stream of nitrogen. 5 µg of nucleic acid is preincubated with 25 µg of oligolysine [average residue length=15 residues] at 30° C., for 30 min, and then added to the lipid ingredients. The oligolysine/siRNA mixture is then combined with lipids and dispersed in 60 µl DMSO and 1.4 ml buffer (10 mM Tris, 0.1 M KCl, 1 mM EDTA pH 8.0). Sodium cholate, 140 µl (100 mg/ml stock in [0.15 M NaCl 0.003 M KCl, 0.15 M $KH_2PO4$, pH 7.4, designated as PBS]) is added to produce a final PC to cholate molar ratio of ~1:1.6. Apo A-I (12.7 mg/ml) in 0.4 ml of PBS is added to the mixture and the final volume is adjusted to 2 ml with PBS. The lipid/protein/cholate mixture is then incubated for 12 hrs at 4° C., followed by dialysis against 2 liter of PBS, for two days, with three buffer changes. The nucleic acid incorporation is determined by the RiboGreen assay system (Invitrogen) for the respective nucleic HDL-nucleic acid formulations.

The reagents, including positively charged amino acid sequence, apolipoprotein, and lipids can be obtained from commercial sources, or can be chemically synthesized, or can be obtained from natural sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol. The particles of the present invention can be dried, and reconstituted for later use. The dried particles can be stored for later use.

B. Nucleic Acids

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. A nucleobase may be comprised in a nucleside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as flourescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes olignucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

5. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/ 01219). A peptide nucleic acid generally comprises one or more nucleotides or nucleosides that comprise a nucleobase moiety, a nucleobase linker moeity that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyimide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR™, to reduce false positives and discriminate between single base mutants, as described in U.S. Pat. No. 5,891,625. Other modifications and uses of nucleic acid analogs are known in the art, and it is anticipated that these techniques and types of nucleic acid analogs may be used with the present invention. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

6. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

7. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

8. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

C. Therapeutic Gene Silencing

Since the discovery of RNAi by Fire and colleagues in 1981, the biochemical mechanisms have been rapidly characterized. Long double stranded RNA (dsRNA) is cleaved by Dicer, which is an RNAaseIII family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). MiRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004). While many of these approaches are successful for in vitro studies, in vivo delivery poses additional challenges based on the complexity of the tumor microenvironment.

In vivo siRNA delivery using neutral liposomes in an orthotopic model of advanced ovarian cancer has been described (Landen et al., 2005, which is incorporated herein by reference in its entirety). For example, intravenous injection of the DOPC-siRNA complex allowed a significantly greater degree of siRNA deposition into the tumor parenchyma than either delivery with cationic (positively charged) liposomes (DOTAP) or unpackaged "naked" siRNA. While the DOPC formulation delivered siRNA to over 30% of cells in the tumor parenchyma, naked siRNA was delivered only to about 3% of cells, and DOTAP delivered siRNA only to tumor cells immediately adjacent to the vasculature.

Although siRNA appears to be more stable than antisense molecules, serum nucleases can degrade siRNAs (Leung and Whittaker, 2005). Thus, several research groups have developed modifications such as chemically stabilized siRNAs with partial phosphorothioate backbone and 2'-0-methyl sugar modifications or boranophosphate siRNAs (Leung and Whittaker, 2005). Elmen and colleagues modified siRNAs with the synthetic RNA-like high affinity nucleotide analogue, Locked Nucleic Acid (LNA), which significantly enhanced the serum half-life of siRNA and stabilized the structure without affecting the gene-silencing capability (Elmen et al., 2005). Alternative approaches including chemical modification (conjugation of cholesterol to the 3' end of the sense strand of siRNA by means of a pyrrolidine linker) may also allow systemic delivery without affecting function (Soutschek et al., 2004). Apsects of the present invention can use each of these modification strategies in combination with the compositions and methods described.

D. Therapeutic Nucleic Acids

The present invention concerns methods of delivery of therapeutic nucleic acids, wherein the nucleic acid encodes a therapeutic protein, polypeptide, or peptide. Any nucleic acid or gene known to those of ordinary skill in the art is contemplated by the present invention. The term "gene" is used for simplicity to refer to a functional protein, polypeptide, or peptide-encoding unit and does not necessarily refer to a genomic fragment including the exon and introns of genomically encoded gene. Thus, gene is used to denote a nucleic acid that includes a nucleotide sequence that includes all or part of a nucleic acid sequence associated with a particular genetic locus. Thus, in some embodiments, the therapeutic nucleic acid encodes a functional protein, polypeptide, or peptide-encoding unit that has therapeutic applications.

A "therapeutic gene" is a gene which can be administered to a subject for the purpose of treating or preventing a disease. For example, a therapeutic gene can be a gene administered to a subject for treatment or prevention of diabetes or cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus1, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

In certain embodiments of the present invention, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell.

Examples of tumor suppressor nucleic acids within this definition include, but are not limited to APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at www.cise.ufl.edu/~yy1/HTML-TS-GDB/Homepage.html. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the present invention.

In certain embodiments of the present invention, the therapeutic gene is a gene that induces apoptosis (i.e., a pro-apoptotic gene). A "pro-apoptotic gene amino acid sequence" refers to a polypeptide that, when present in a cell, induces or promotes apoptosis. The present invention contemplates inclusion of any pro-apoptotic gene known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. One of ordinary skill in the art would be familiar with pro-apoptotic genes, and other such genes not specifically set forth herein that can be applied in the methods and compositions of the present invention.

The therapeutic gene can also be a gene encoding a cytokine. The term 'cytokine' is a generic term for proteins released by one cell population which act on another cell as intercellular mediators. A "cytokine" refers to a polypeptide that, when present in a cell, maintains some or all of the function of a cytokine. This definition includes full-length as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10 IL-11, IL-12; IL-13, IL-14, IL-15, IL-16, IL-17, IL-18, IL-19, IL-20, IL-24 LIF, G-CSF, GM-CSF, M-CSF, EPO, kit-ligand or FLT-3.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerebrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of about 5 to about 12000 or more nucleotides, nucleosides, or base pairs.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

Encompassed within the definition of "therapeutic gene" is a "biologically functional equivalent" therapeutic gene. Accordingly, sequences that have about 70% to about 99% homology of amino acids that are identical or functionally equivalent to the amino acids of the therapeutic gene will be sequences that are biologically functional equivalents provided the biological activity of the protein is maintained.

E. Inhibition Of Gene Expression

In certain embodiments of the present invention, the HDL-nucleic acid particle includes a nucleic acid that is a siRNA. siRNA (also known as siNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90 to 100, 150, 200, 250, 300, 350, 400, 450, 500 or more contiguous nucleobases, including all ranges therebetween. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

Agents of the present invention useful for practicing the methods of the present invention include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998), but is widespread in other organisms, ranging from trypanosomes to mouse. Depending on the organism being discussed, RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80, 85, 90, 95, 98,% or even 100% identity between the sequence of the siRNA and the gene to be inhibited. Sequences less than about 80% identical to the target gene are substantially less effective. Thus, the greater homology between the siRNA and the STAT gene to be inhibited, the less likely expression of unrelated genes will be affected.

In addition, the size of the siRNA is an important consideration. In some embodiments, the present invention relates to siRNA molecules that include at least about 19-25 nucleotides, and are able to modulate the MMP expression. In the context of the present invention, the siRNA is preferably less than 500, 200, 100, 50 or 25 nucleotides in length. More preferably, the siRNA is from about 19 nucleotides to about 25 nucleotides in length.

siRNA can be obtained from commercial sources, natural sources, or can be synthesized using any of a number of techniques well-known to those of ordinary skill in the art. For example, one commercial source of predesigned siRNA is Ambion®, Austin, Tex. Another is Qiagen® (Valencia, Calif.). An inhibitory nucleic acid that can be applied in the compositions and methods of the present invention may be any nucleic acid sequence that has been found by any source to be a validated downregulator of an Id protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 20040019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of a gene of interest by at least 10%, 20%, 30%, or 40%, more preferably by at least 50%, 60%, or 70%, and most preferably by at least 75%, 80%, 90%, 95% or more.

F. Treatment Of Disease

1. Definitions

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a nucleic acid that inhibits the expression of a gene that encodes an MMP and a neutral lipid for the purposes of minimizing the growth or invasion of a tumor.

A "subject" refers to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A "disease" or "health-related condition" can be any pathological condition of a body part, an organ, or a system resulting from any cause, such as infection, genetic defect, and/or environmental stress. The cause may or may not be known.

In some embodiments of the invention, the methods include identifying a patient in need of treatment. A patient may be identified, for example, based on taking a patient history, based on findings on clinical examination, based on health screenings, or by self-referral.

2. Diseases

The present invention can find application in the treatment of any disease for which delivery of a therapeutic nucleic acid to a cell or tissue of a subject is believed to be of therapeutic benefit. Examples of such diseases include hyperproliferative diseases, inflammatory diseases, infectious diseases, degenerative diseases, and autoimmune diseases. In particular embodiments, the disease is cancer.

For example, a siRNA that binds to a nucleic acid may be administered to treat a cancer. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, and/or a neurodegenerative disease).

G. Pharmaceutical Preparations

Where clinical application of the particles of the present invention is undertaken, it will generally be beneficial to prepare the particles as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. For animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound, such as a nucleic acid. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 μg/kg/body weight to about 100 mg/kg/body weight, about 5 microgram/kg/body weight to about 500 milligram/kg/body weight, etc., can be administered.

A nucleic acid may be administered in a dose of 1, 2, 3, 4, 5, 6, 7, 8, 9, 10, 15, 20, 25, 30, 40, 50, 60, 70, 80, 90, 100 or more μg of nucleic acid per dose. Each dose may be in a volume of 1, 10, 50, 100, 200, 500, 1000 or more μl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal, topical, or aerosol.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

H. Combination Treatments

In certain embodiments, the compositions and methods of the present invention involve and HDL-nucleic acid particle as set forth herein with a second or additional therapy. Such therapy can be applied in the treatment of any disease for which treatment with the HDL-nucleic acid particle is contemplated. For example, the disease may be a hyperproliferative disease, such as cancer.

The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with a therapeutic nucleic acid, such as an inhibitor of gene expression, and a second therapy. A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitor of gene expression; 2) an anti-cancer agent, or 3) both an inhibitor of gene expression and an anti-cancer agent. Also, it is contemplated that such a combination therapy can be used in conjunction with a chemotherapy, radiotherapy, surgical therapy, or immunotherapy.

A therapeutic nucleic acid as set forth in the HDL formulations set forth herein may be administered before, during, after or in various combinations relative to an anti-cancer treatment. The administrations may be in intervals ranging from concurrently to minutes to days to weeks. In embodiments where the inhibitor of gene expression is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below a therapeutic nucleic acid is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the therapeutic nucleic acid and the anti-cancer therapy, as described herein.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas. Examples of these agents have been previously set forth.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and read ministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

I. Kits and Diagnostics

In various aspects of the invention, a kit is envisioned containing therapeutic agents and/or other therapeutic and delivery agents. In some embodiments, the present invention contemplates a kit for preparing and/or administering a therapy of the invention. The kit may comprise one or more sealed vials containing any of the pharmaceutical compositions of the present invention. In some embodiments, the HDL is in one vial, and the nucleic acid component is in a separate vial. The kit may include one or more lipid components, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

J. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Example of Protocol for rHDL/siRNA Preparation

Nuclease free water was used throughout these procedures, including for the preparation of buffer solutions.

Annealing of sense and anti-sense oligonucleotide strands. Samples of the siRNA are suspended in 100 µl Annealing Buffer (10 mM HEPES, 100 mM potassium acetate, 2 mM magnesium acetate, pH 7.4). Heat for 1 min at 90° C. in a water bath followed by incubation for 1 hr at 37° C.

Formation of the siRNA/oligolysine complex. The conditions for the optimum incorporation of a generic siRNA into rHDL were established by preliminary studies.

|  | RNA (µg) | Oligolysine (µg) |
|---|---|---|
| Control | 5 | 0 |
| Sample | 5 | 5 |

Incubate the mixture at 30° C. for 30 min and prepare siRNA oligolysine complex.

rHDL/siRNA assembly. A mixture of egg yolk phosphatidyl choline (PC) in $CHCl_3$ with free cholesterol, cholesteryl oleate (CE), and 5 µg of siRNA was prepared with a molar ratio of Apo A-I: cholesterol:cholesteryl oleate:PC=1:5:1.3: 115M. The volume of the mixture of lipids (PC, C, CE) and siRNA is reduced under a stream of $N_2$ and then dispersed in 60 µl DMSO and 1.4 ml buffer (10 mM Tris, 0.1 M KCl, 1 mM EDTA, pH 8.0). Sodium cholate (140 µl of a 100 mg/ml cholate stock in PBS [0.15M NaCl, 0.003 M KCl, 0.15 M $KH_2PO_4$, pH 7.4]) was added to produce a suspension with a final PC to cholate molar ratio of 1:1.6. Subsequently, a solution of apolipoprotein A-I (apo-A-I), 12.7 mg/ml in 0.4 ml of PBS was added and the final volume was adjusted to 2 ml with PBS. The lipid/protein/cholate/siRNA mixture was then incubated overnight at 4° C., followed by dialysis against 2 liters of PBS, for two days, with three buffer changes. On the following day, the dialysate was recovered, centrifuged to remove particular matter and the RNA content was measured using the ribogreen assay (Quani-iT Ribogreen Kit, Molecular Probes cat #R11490).

Table 1 shows the RNA content of rHDL/siRNA recovered following dialysis.

TABLE 1

| Sample | RNA before dialysis (ng) | RNA after dialysis** (ng) | Recovery (%) after dialysis |
|---|---|---|---|
| Control (no oligolysine) | 448 | 272 | 61 |
| Sample 1 (oligolysine) | 417 | 348 | 83 |

**the siRNA recovered, following the extensive dialysis process represents the RNA molecules that are encased in a macromolecular complex (rHDL/siRNA). See FIG. 1.

Example 2

Delivery of siRNA Using rHDL/siRNA Nanoparticles

Figure 4:
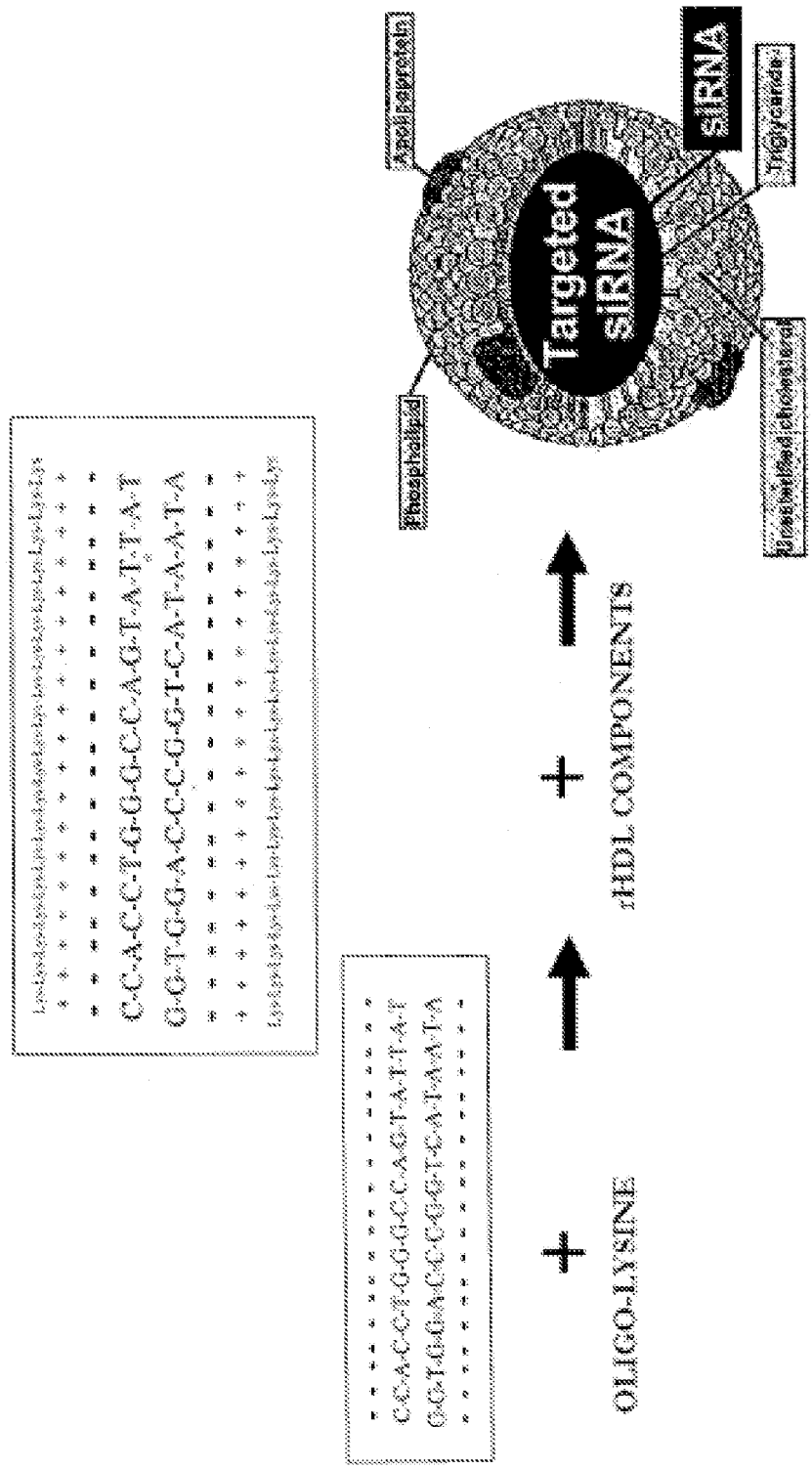
FIG. 4. Assembly of the siRNA/rHDL nanocomplex. Shown is a DNA sequence encoding the FAK-siRNA. The FAK-siRNA sequence is SEQ ID NO:2, and the DNA sequence encoding said sequence is SEQ ID NO:4 and its complement is SEQ ID NO:5. Also shown is a poly-lysine sequence (SEQ ID NO:6).
Figure 5:
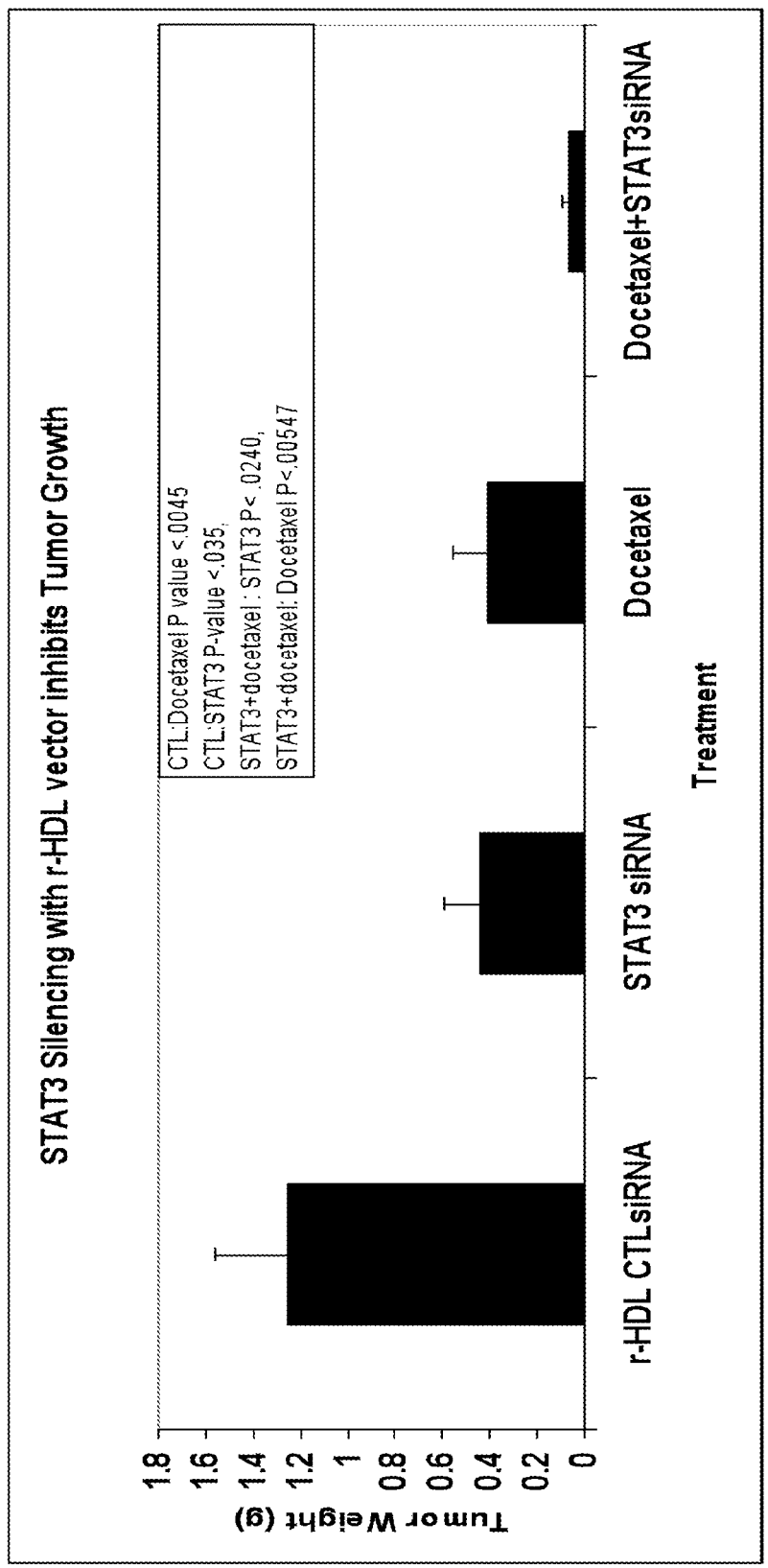
FIG. 5. STAT3 silencing with rHDL vector inhibits tumor growth.

The modified rHDL delivery system described herein (FIG. 2) is appropriate for the delivery of all types of nucleic acids. The delivery system requires the modification of HDL-containing liposomes to suppress the ionic character of nucleic acid, such as siRNA (FIG. 3). FIG. 2 illustrates the approach, using the positively charged oligolysine units (MW 500-2000) for the efficient packaging and subsequent delivery of the focal adhesion kinase (FAK)-siRNA that was used in the present studies to demonstrate silencing of the FAK expression (FIG. 4). Fluorescently-labeled siRNA has been successfully delivered into tumor, liver, kidney, spleen, and lung of nude mice by intravenous injection. In vivo Alexa-555 siRNA distribution in HeyA8 tumor tissue was examined after a single siRNA dose. Tumor samples were exposed to anti-f4/80 antibody to detect scavenging macrophages and Alexa 488-tagged secondary antibody. Alexa 555 siRNA was seen in both tumor cells and surrounding macrophages. Moreover, focal adhesion kinase (FAK) has been silenced in vivo using FAK-targeted siRNA/rHDL nanoparticles in ovarian HeyA8 tumors after a single injection.

Example 3

Preparation and Characterization of rHDL/Paclitaxel Particles

Preparation of Recombinant ApoA-I. Recombinant Apo-A-I is prepared as described in Ryan et al., 2003, and was used to prepare rHDL/paclitaxel complexes. The particles are prepared by a process involving cholate dialysis to produce a spherical structure with the pharmaceutical enclosed in the interior hydrophobic core region. The lipid mixture (egg yolk phosphatidylcholine, cholesterol and cholesteryl oleate in the ratio of 3.8:1:88.5) and 2 mg paclitaxel is dried under $N_2$ to a thin film and dispersed in dimethylsulfoxide and subsequently in 1.4 ml of 10 mM Tris, 0.1 M KCl, 1 mM EDTA, pH 80). Sodium cholate, 140 μl (100 mg/ml stock in [0.15 M NaCl, 0.003 M KCl, 0.15 M $KH_2PO_4$, pH 74, designated as PBS]) is added to produce mixtures with a final PC to cholate molar ratio of about 1:1.6. Apo A-I (12.7 mg/ml) in 0.4 ml of PBS is added to this mixture and the final volume is adjusted to 2 ml with PBS. The lipid/potein/cholate mixture is then incubated for 12 hrs at 4 degrees C., followed by dialysis (2 liter of PBS, for two days) with three buffer changes using $^3$H-cholate as a tracer, <2% of the cholate remained in the rHDL/drug preparations while over 60% of the paclitaxel remained associated with the rHDL delivery particles.

Storage and Stability. Particles of the invention can be stored at 4° C. and remain stable for at least 60 days.

Example 4

Targeted Delivery of Small Interfering RNA Using rHDL Nanoparticles

Materials and Methods rHDL nanoparticle preparation and siRNA incorporation. This process involves the suppression of the ionic charges in the siRNA moiety before incorporation into the rHDL nanoparticles. Briefly, a mixture of lipids [cholesterol (C)/cholesteryl oleate (CE)/egg yolk phosphatidyl choline (PC), molar ratio of 1:5:1.3:115] is dried under a stream of nitrogen. siRNA (5 μg) is preincubated with 25 μg of oligolysine [average mw 500-2000] (30° C.), for 30 min, and then added to the lipid ingredients. The oligolysine/siRNA mixture is then combined with lipids and dispersed in 60 μl DMSO and 1.4 ml buffer (10 mM Tris, 0.1 M KCl, 1 mM EDTA pH 8.0). Sodium cholate, 0.14 ml (100 mg/ml stock in [0.15 M NaCl 0.003 M KCl, 0.15 M $KH_2PO4$, pH 7.4, designated as PBS]) is added to produce a final PC to cholate molar ratio of ~1:1.6. Apo A-I (12.7 mg/ml) in 0.4 ml of PBS is added to the mixture and the final volume is adjusted to 2 ml with PBS. The lipid/protein/cholate mixture is then incubated for 12 hrs at 4° C., followed by dialysis against 2 liter of PBS, for two days, with three buffer changes. This siRNA formulation method has been equally effective for several of the tested siRNAs. The stability of the siRNA/rHDL preparation will be assessed by assessing the distribution of siRNA released during cell culture from the siRNA/rHDL formulations, subsequent to intravenous injection of the respective preparations, by the ribogreen RNA Quantitation Kit (Invitogen).

Cell lines and culture conditions. HeyA8, SKOV3ip1, and HeyA8-MDR cell lines were grown as previously described (Thaker et al., 2005).

Orthotopic mouse model. The 10- to 12-week-old female athymic nude mice were obtained from the US National Cancer Institute. All experiments were approved by the Institutional Animal Care and Use Committee of the M.D. Anderson Cancer Center. Treatment was given according to the following groups (n=10 per group): 1) Control siRNA/rHDL alone, 2) Control siRNA/rHDL+docetaxel, 3) STAT3 siRNA/rHDL, and 4) STAT3 siRNA/rHDL plus docetaxel. Tumor cells for appropriate ovarian cancer mouse models (HeyA8, 2.5×105; SKOV3ip1 and HeyA8MDR, 1.0×106) were injected intraperitoneally into mice on day 0. Mice randomized into appropriate groups on day 7 when tumors had been established and were palpable. After 3-5 weeks of treatment (depending on the model), mice were necropsied and tumors were harvested.

Small interfering RNA (siRNA). Specific siRNAs targeted against Stat3_7 (target sequence 5'-GCCUCUCUGCA-GAAUUCAA-3'; SEQ ID NO:1), FAK (target Sequence 5'-CCACCUGGGCCAGUAUUAU-3'; SEQ ID NO:2) and control siRNA targeted against (target sequence:5'-UUCUC-CGAACGUGUCACGU-3'; SEQ ID NO:3) were purchased from Sigma-Aldrich Corporation, (Woodland, Tex.). These were incorporated into r-HDL nanoparticles, as previously described (Mooberry et al., 2009). 5 ug of r-HDL incorporated siRNA was injected intraperitoneally twice weekly. For in vitro studies, mRNA-specific or nonspecific (control) siRNA was incorporated into Qiagen RNAiFect transfection agent (1 ug of siRNA to 3 uL of RNAiFect). Only 70% to 80% confluent SKOV3ip1 cells were utilized. Cells were first transfected with STAT3 siRNA. Twenty-four hours after transfection, media was changed to standard siRNA-free media and cells were treated with docetaxel (see below for details).

Immunohistochemistry. Paraffin sections for CD31 (1:800 dilution, Pharmingen), were stained at 4° C. Control samples were exposed to secondary antibody alone, and they did not show any nonspecific staining These details have been reported previously (Halder et al., 2006; Thaker et al., 2005). To quantify MVD, five random 0.159 mm2 fields at 100× magnification for each tumor were examined, and microvessels within those fields were counted (Thaker et al., 2005). KI-67 staining (cell proliferation index) was conducted on 4-μm-thick formalin-fixed paraffin-embedded epithelial ovarian cancer specimens as described (Merritt et al., 2008). Five random 0.159 $mm^2$ fields were examined at 100× magnification. Percent of Ki-67 positive cells is reported, while the representative figures reported were taken at 200× magnification.

TUNEL Staining. Assessment of apoptosis, frozen sections stained by terminal deoxynucleotidyl transferase-mediated deoxyuridine triphosphate nick-end labeling (TUNEL; green; Promega, Madison, Wis.), was performed as described previously (Shahzad et al., 2009). The samples were counterstained with Hoechst 1:10,000 (Thaker et al., 2005). An apoptotic body was represented by green fluorescence. To quantify apoptotic cells, the number of TUNEL positive cells was calculated in 10 random fields at the original magnification 200× from five separate slides (per group) and averaged.

MTT assay. SKOV3 cell (1.5×105) cells were plated in each well, using 6 well plates. Cells were then transfected with control or STAT3 siRNA overnight. Cells were then trypsenized and plated in 96 well plates. Twelve hours later, cells were treated with docetaxel and reincubated in 37 degrees. Forty-eight hours after docetaxel treatment, the number of viable cells was determined by adding 50 μL of 0.15% 3-(4,5-dimethylthiazol-2-yl)-2,5-diphenyl tetrazolium bromide (MTT; Sigma) to each well. After a 2-hour incubation at 37° C., the medium and MTT were removed, and the remaining cells were reconstituted in 100 μL of dimethyl sulfoxide (Sigma-Aldrich; Woodlands, Tex.). Viable cells were quantified by measuring the absorbance at 570 nm using a uQuant plate reader (Bio-Tek, Winooski, Vt.). Proliferation assays were performed with three replicate wells.

Western blot. After cell lysate was prepared with radioimmune precipitation (RIPA) lysis buffer as previously reported (Landen et al., 2006), protein concentrations were determined using a BCA protein assay reagent kit (Pierce). Twenty μg of cell lysate protein was subjected to 15% SDS-PAGE separation and transferred to a nitrocellulose membrane via wet transfer (Bio-Rad Laboratories). Nonspecific sites were blocked with 10% nonfat milk and incubated with stat3 antibody (1:2500; BD biosciences, CA.) overnight at 4° C. Primary antibody was detected utilizing anti-mouse IgG (GE healthcare, UK) and developed with a chemiluminescence detection kit (PerkinElmer). Beta-actin antibody (1:2000; Sigma) confirmed equal loading.

Fluorescence staining. Fresh frozen tumor tissues were first fixed in acetone for 15 minutes, washed with PBS twice for 5 minutes each, and counter-stained with Hoeschet (1:10, 000).

Reagents. Docetaxel was purchased from Sanofi-Aventis (Bridgewater, N.J.). All in vitro experiments were conducted using 4.0 nM concentration of docetaxel in SKOV3ip1 ovarian cancer cells. These cells were treated with docetaxel after STAT3 gene was silenced using siRNA (as described above) for 48 hours. In In vivo experiments, appropriate groups received treatment with docetaxel starting on day 7, once a week, intraperitoneally at: 50 ug/mouse (HeyA8 and HeyA8-MDR) and 30 ug/mouse (SKOV3). Moreover, 5 ug of STAT3 or control siRNA incorporated into r-HDL nanoparticles was injected twice weekly starting 7 days after tumor cell injection.

Statistics. Continuous variables were compared with the use of the Student t test (between 2 groups) or analysis of variance (for all groups) if normally distributed, and with the use of the Mann-Whitney rank sum test or Kruskal Wallis test (for all groups) if nonparametric. All statistical tests were performed with SPSS software (SPSS Inc, Chicago, Ill.). A probability value of <0.05 on 2-tailed testing was considered significant.

Results

Figure 6A:
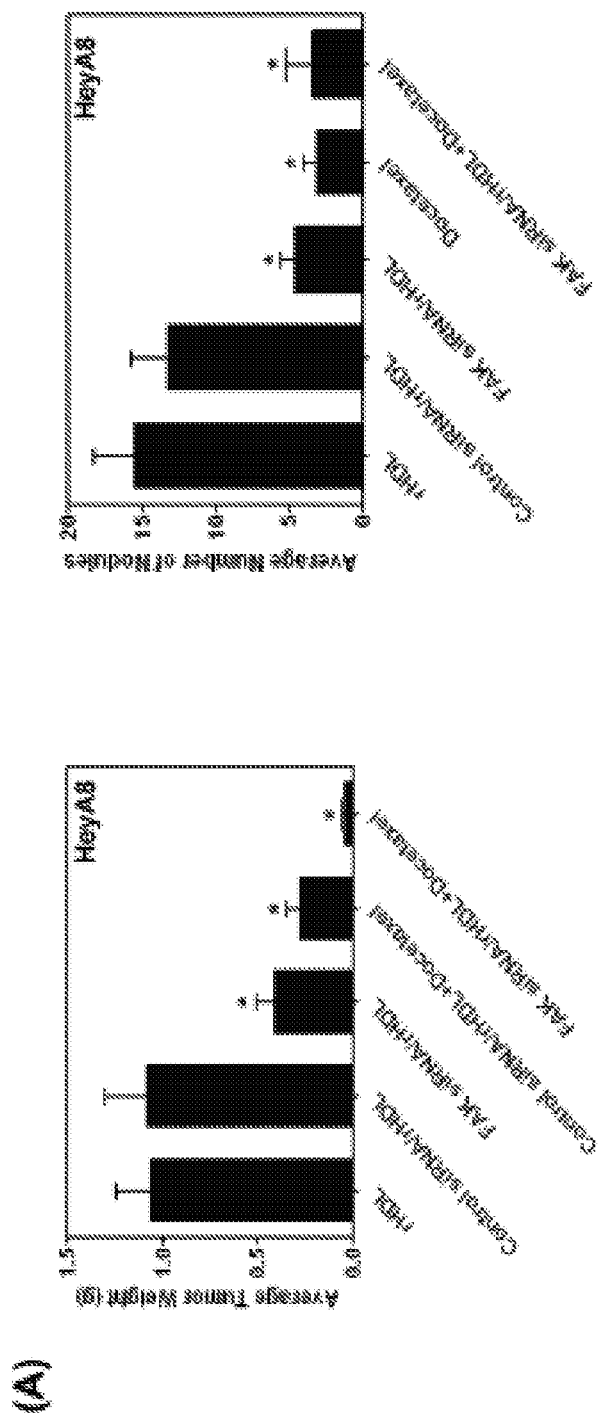
FIG. 6A, 6B, 6C. 6A—Average tumor weight and average number of nodules vs. therapeutic agent; 6B—average tumor weight vs. therapeutic agent in HeyA8, SKOV3, and HeyA8-MDR cells; 6C—Average tumor weight and average number of nodules vs. therapeutic agent in HCT 116 cells. *P<0.05 compared to control siRNA/rHDL.
Figures 6B, 6C:
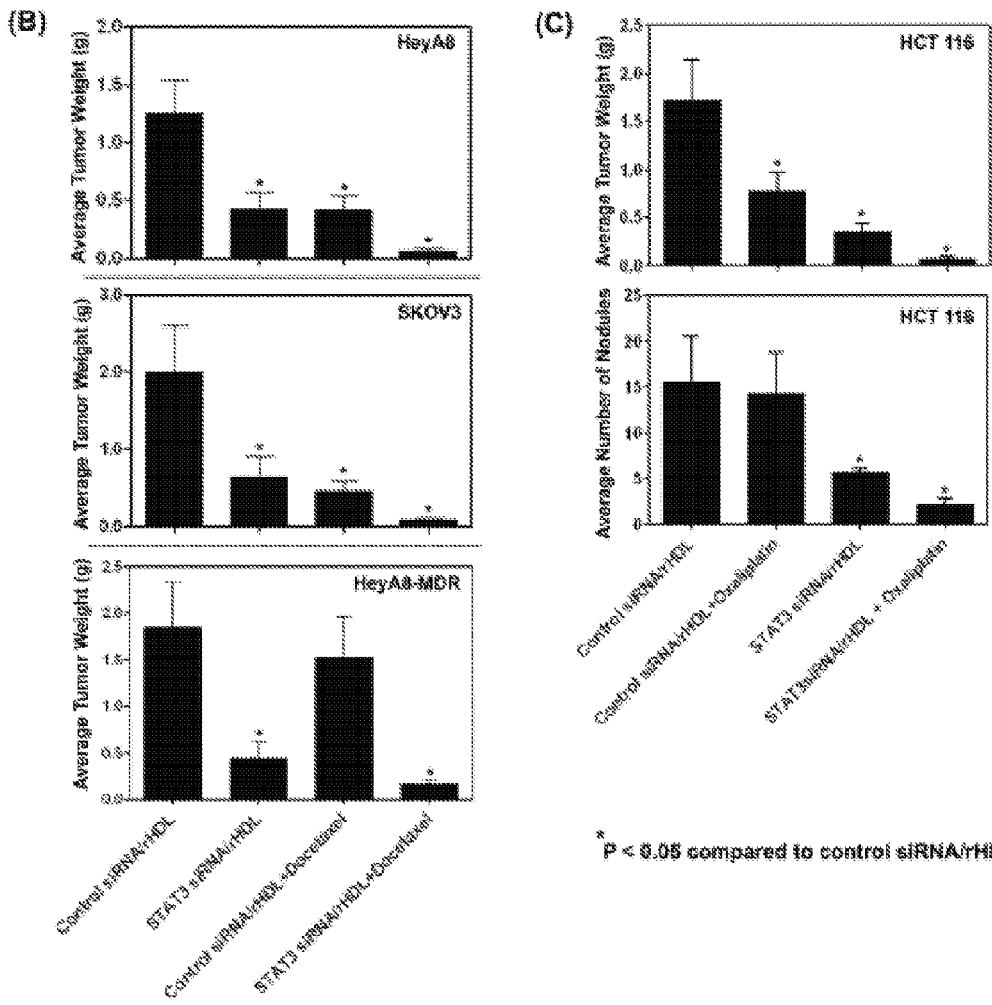

Characterization of rHDL nanoparticles and their selective uptake via SR-B1 receptor. The expression of rHDL receptor, SR-B1, with RT-PCR in normal human organs, breast, ovarian, pancreatic, and colon cancer cell lines was determined (FIG. 6). All of the cancer cell lines tested demonstrated high level of SR-B1 expression. Liver had the highest expression of SR-B1, while normal organs had minimal to no expression of SR-B1. Additionally, fifty human ovarian epithelial tumors were examined for SR-B1 expression using IHC. It was found that 96% of the tumors expressed SR-B1 receptor (FIG. 6). Furthermore, 73% of the tumors had high expression of SR-B1.

Selective delivery of rHDL nanoparticles in vivo. Given the high expression of HDL receptor in tumors compared to the normal tissues, an ovarian tumor cell line with high expression of SR-B1 (SKOV3ip1) was used to access the selective delivery-potential of siRNA to the tumor and organs in nude mice. Fluorescently tagged siRNA was incorporated into rHDL nanoparticles and injected IV or IP. An evenly distributed delivery of siRNA in tumor was observed. Interestingly, these tumors displayed high level of fluorescence compared to normal organs. To determine whether the rHDL particle delivery was receptor mediated, organs from mice that were treated with florescent tagged siRNA/rHDL were analyzed. Liver demonstrated high uptake of rHDL particles while no delivery was noted in brain, heart, lung, kidney, or spleen. Additionally, there was no difference between IP versus IV delivery.

Next, to determine the efficiency of the rHDL nanoparticle delivery system, studies were conducted to assess whether a single dose of (5 ug) specific siRNA against a previously targeted gene, FAK (Focal Adhesion Kinase) (Halder et al., 2006) would silence the FAK gene expression. The results indicate that FAK silencing was best seen 4 days after a single intraperitoneal injection of FAK targeted siRNA that was incorporated into rHDL nanoparticles in nude mice and FAK was only starting to recover by day 6 at the protein level. Hence providing evidence that r-HDL not only penetrates deep into the ovarian tumors, it also efficiently releases the specific siRNA inside tumor cells leading to an effective down-regulation of its target gene.

Prior to conducting long term therapeutic studies with this approach, studies were conducted to determine whether STAT3 can be targeted using siRNA incorporated into rHDL nanoparticles. In order to determine an effective dose required to silence STAT3 protein in vivo, 2.5 ug, 5.0 ug, or 10.0 ug of STAT3 siRNA/rHDL was injected in SKOV3ip1 tumor bearing mice (FIG. 6). At 48 h after a single injection of 5.0 μg of siRNA, a complete silencing of STAT3 protein was demonstrated. Hence, it was decided to use this does for further studies.

Figure 7:
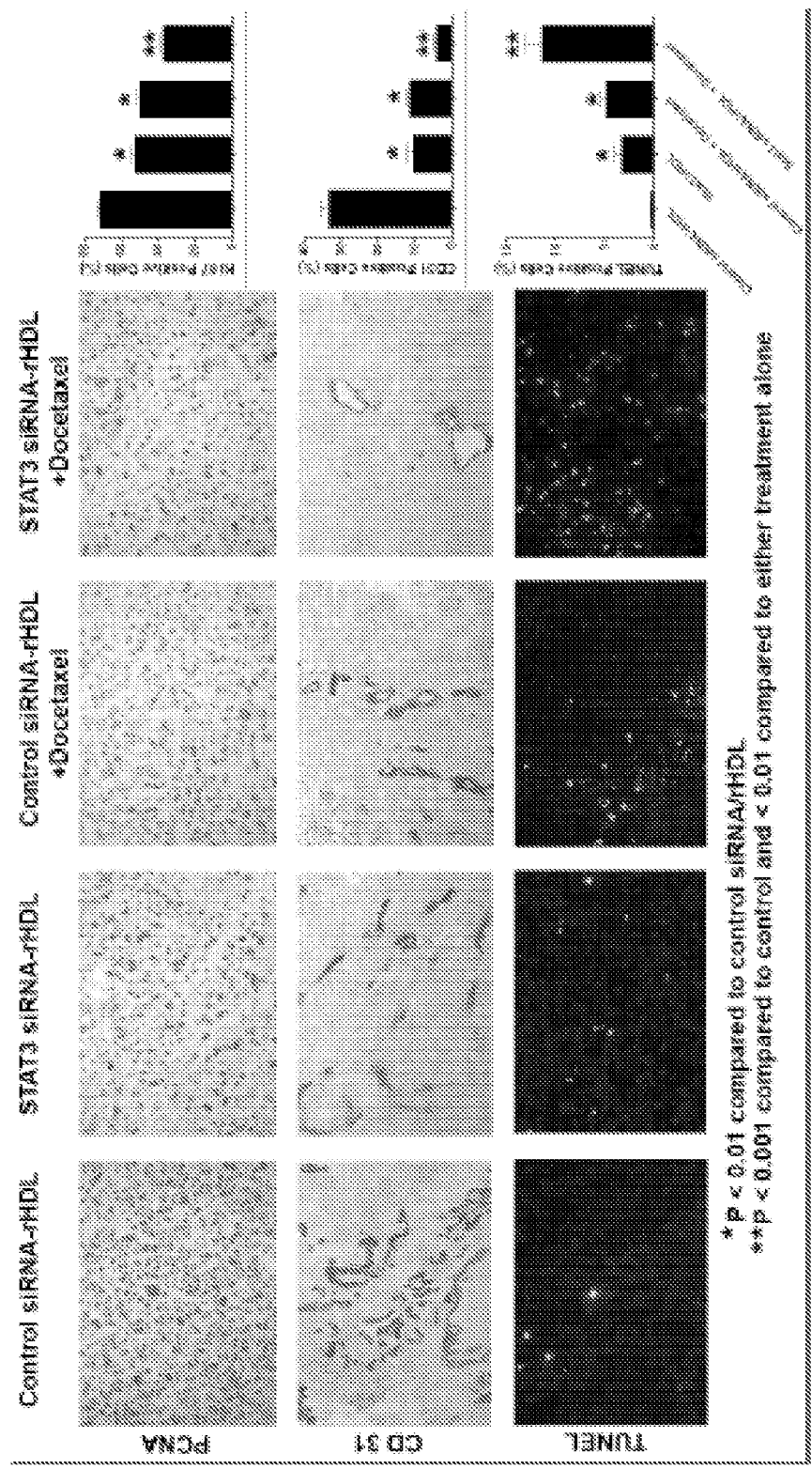
FIG. 7. Analysis of percent KI positive cells, CD31 positive cells, and Tunel positive cells vs. therapeutic regimen. *P<0.01 compared to control siRNA/rHDL; **P<0.001 compared to control and <0.01 compared to either treatment alone.

Effect of STAT3 or FAK gene targeting on tumor growth and metastasis. After successfully silencing STAT3 or FAK genes in vivo, studies were conducted to determine whether targeting either FAK or STAT3 will enhance the therapeutic efficacy of docetaxel (FIG. 7). For proof-of-concept studies, FAK was targeted using siRNA incorporated into rHDL nanoparticles in a highly aggressive orthotopic mouse model of ovarian carcinoma (HeyA8). FAK or docetaxel treatment resulted in 62 to 74% reduction in tumor growth (P<0.01, 0.005, respectively) and the combination treatment resulted in the greatest reduction in tumor growth (by 96%; P<0.002) and tumor metastasis (by 74%; P<0.015). Additionally, there were no differences in tumor growth or metastasis between mice that were treated with empty rHDL nanoparticles versus those treated with control siRNA/rHDL.

Studies were conducted to determine the effects of STAT3 targeting in vivo. Mice were either treated with STAT3 siRNA/r-HDL alone or in combination with docetaxel using three well characterized ovarian cancer orthotopic mouse models. In HeyA8 model, STAT3 siRNA/rHDL or docetaxel treatment alone reduced tumor growth by 62% (P<0.04, both) and tumor metastasis by 68 to 77% (P<0.04, 0.03, respectively) compared to the control group (FIG. 7). Combination treatment with STAT3 siRNA/rHDL and docetaxel resulted in the most significant reduction in tumor growth (by 92%, P<0.003) and metastasis (by 96%, P<0.009) compared to control. Additionally, these finding were validated in another highly aggressive orthotopic ovarian cancer mouse model (SKOV3ip1). In this study, STAT3 siRNA/rHDL or docetaxel treatment alone reduced tumor growth by 68 to 78% compared to control group (P<0.04, 0.03, respectively). Combined STAT3 siRNA/rHDL and docetaxel treatment resulted in over 95% reduction in tumor growth (P<0.001) and an 80% decrease in the number of tumor nodules compared to control siRNA/rHDL treated mice.

Given that STAT3 is known to play a role in chemoresistance (Shen et al., 2001; Catlett-Falcone et al. 1999; Zushi et al., 1998; Masuda et al., 2002), whether the efficacy of docetaxel can be enhanced by combining docetaxel treatment with STAT3 gene targeting was next evaluated. In the multidrug resistant model of ovarian carcinoma (HeyA8MDR), docetaxel treatment alone failed to generate any significant effect on tumor growth (17%, P=0.5), while STAT3 siRNA/rHDL monotherapy resulted in a 76% reduction in tumor growth (P<0.01). Interestingly, the combination treatment of docetaxel with STAT3 siRNA/rHDL resulted in the greatest reduction in tumor growth compared to control siRNA/rHDL treatment alone (by 91%, P<0.001) or to docetaxel treatment alone (by 89%, P<0.001). Similar affects were also seen on tumor metastasis.

To examine whether siRNA incorporated into rHDL nanoparticles can be efficiently delivered in another tumor type, the therapeutic effect of STAT3 gene silencing in a well characterized mouse model of metastatic colon cancer (HCT116) (Kopetz et al., 2009) that has a high baseline expresses of SR-B1 was determined (FIG. 7). Here, oxaliplatin or STAT3 siRNA/rHDL treatment alone resulted in 55-79% reduction in tumor growth (P<0.01, both). The combination of oxaliplatin and STAT3 siRNA/rHDL resulted in the most significant reduction in tumor growth (96%; P<0.01) and tumor metastasis (86%, P<0.01) compared to controls.

Effect of STAT3 targeting on tumor microenvironment. Ki-67 staining was performed on tumors from SKOV3ip1 model that resulted in the highest response rate to the combination treatment. STAT3 gene targeting alone resulted in 26% reduction in cell proliferation (P<0.01), while docetaxel treatment alone inhibited tumor cell proliferation by 30% (P<0.01). The combination of STAT3 siRNA/rHDL and docetaxel reduced tumor cell proliferation by 48% (P<0.01) compared with control group (FIG. 7).

In order to ascertain the effects of STAT3 silencing on tumor associated angiogenesis, CD 31 staining on fresh frozen tumor samples from all four treatment groups (FIG. 7) was determined along with microvessel density (MVD). The results indicate that STAT3 siRNA/rHDL or docetaxel alone results in 69 to 66% reduction (P<0.01, both) in MVD. The STAT3 siRNA/rHDL and docetaxel combination treatment resulted in 88% reduction in tumor associated vessel counts (P<0.001) compared with control siRNA/rHDL treatment.

STAT3 is known to increase cell survival and inhibit apoptosis (Shen et al., 2001; Catlett-Falcone et al., 1999; Zushi et al., 1998; Masude et al., 2002). To assess whether STAT3 knockdown would enhance the efficacy of docetaxel treatment by enhancing its ability to produce apoptosis., fluorescents labeled TUNEL staining was performed on fresh frozen tumor tissues from the SKOV3ip1 ovarian cancer treatment model. STAT3 gene targeting with siRNA incorporated into rHDL nanoparticles or docetaxel treatment alone resulted in 8 to 12 folds increases in apoptosis compared to control group (P<0.001, both). Combination treatment with STAT3 siRNA/rHDL and docetaxel resulted in a 30-fold increase in tumor cell apoptosis compared to the controls (P<0.001).

Effects of In vitro STAT3 silencing on cell survival and apoptosis. SKOV3ip1 ovarian cancer cells that were transfected with STAT3 siRNA were treated with docetaxel in escalating doses. Using a MMT assay, it was demonstrated that STAT3 silencing lowered the IC 50 values of docetaxel significantly when compared to docetaxel treatment.

Additionally, to determine the effects of in vitro STAT3 targeting on apoptosis, STAT3 gene was silenced in SKOV3ip1 ovarian cancer cells using an siRNA targeted against STAT3 and followed by treatment with docetaxel (4 nM). 48 hours after docetaxel treatment, the extent of cell death secondary to apoptosis was analyzed after Annexin-V PE/7AAD staining with flow cytometry. The results indicate that STAT3 siRNA and docetaxel treatments alone resulted in increased apoptosis (by 3 and 5.2 fold, respectively; P<0.05, both), while combination treatment resulted in 7.7 folds higher apoptosis compared to control (P<0.05). Moreover, compared to docetaxel treatment alone, the addition of STAT3 siRNA resulted in 41% greater apoptosis (P<0.05).

Effect of STAT3 Silencing on Gene Expression profile of Ovarian Tumor Cells. STAT3 knockdown using siRNA targeted against STAT3, microarray analysis using Illumina platform was performed There were 460 genes that were identified to have differential expression levels between the control and STAT3 targeted group. Data was then analyzed using ingenuity-pathway assistance and 32 genes that were involved in cell survival and apoptosis were chosen (Table 1). From this list, 12 genes that were most significantly altered with STAT3 silencing were validated using quantitative Real-time (RT) PCR (Table 2).

TABLE 2

Effect of Stat3 Silencing on Tumor Cell Apoptosis Related Genes

| Gene | Fold Change |
| --- | --- |
| ALOX5 | 1.43 |
| ATF6 | 0.44 |
| BAX | 1.49 |
| BCL6 | 0.72 |
| BEX2 | 1.46 |
| CAV1 | 0.75 |
| CD24 | 0.73 |
| CDCP1 | 0.73 |
| CTGF | 0.62 |
| CYR61 | 0.68 |
| DKK1 | 0.72 |
| DUSP1 | 0.74 |
| ETS2 | 0.56 |
| FGF2 | 0.68 |
| FOS | 0.72 |
| HM OX1 | 1.79 |
| IGFBP3 | 0.45 |
| IL-6 | 0.61 |
| IL-1B | 0.55 |
| KITLG | 0.66 |
| NFKBIZ | 0.65 |
| NQO1 | 0.55 |
| NRP1 | 0.67 |
| PLAUR | 0.72 |
| PMAIP1 | 0.69 |
| PMEPA1 | 0.71 |
| PRKRA | 0.68 |
| RASA1 | 0.68 |
| RTN1 | 1.37 |
| SFRP1 | 0.55 |
| SGK1 | 0.68 |
| SPARC | 0.7 |
| SPP1 | 0.77 |
| STAT3 | 0.23 |
| TCF3 | 0.71 |
| TNFRSF11B | 0.61 |
| TNFSF10 | 0.7 |
| XBP1 | 0.74 |

\* \* \* \* \*

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,816,571
U.S. Pat. No. 4,870,287

U.S. Pat. No. 4,959,463
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,331
U.S. Pat. No. 5,714,331
U.S. Pat. No. 5,714,606
U.S. Pat. No. 5,719,262
U.S. Pat. No. 5,736,336
U.S. Pat. No. 5,739,169
U.S. Pat. No. 5,760,395
U.S. Pat. No. 5,763,167
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,801,005
U.S. Pat. No. 5,824,311
U.S. Pat. No. 5,830,880
U.S. Pat. No. 5,846,945
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
U.S. Pat. No. 6,506,559
U.S. Pat. No. 6,573,099
U.S. Pat. No. 6,673,611
U.S. Appln. Publn. 2002/0168707
U.S. Appln. Publn. 2003/0051263
U.S. Appln. Publn. 2003/0055020
U.S. Appln. Publn. 2003/0159161
U.S. Appln. Publn. 2004/0064842
U.S. Appln. Publn. 2004/0265839
U.S. Appln. Publn. 20040019001
U.S. application Ser. No. 117,363
Ajees et al.; *Proc. Natl. Acad. Sci. USA*, 103:2126-31, 2006.
Akhtar and Benter, *J. Clin. Invest.*, 117(12):3623-32.2007
Alexande et al., *Biochemistry*, 44:5409-19, 2005.
Allen, *Trends Pharmacol. Sci.*, 15:215-220, 1994.
Anantharamaiah et al., *Adv. Exp. Med. Biol.*, 285:131-40, 1991.
Austin-Ward and Villaseca, *Revista Medica de Chile*, 126(7): 838-845, 1998.
Bergers et al., *Pharm. Res.*, 10:1715-1721, 1993.
Bukowski et al., *Clinical Cancer Res.*, 4(10):2337-2347, 1998.
Chonn et al., *Curr. Opinion in Biotech.*, 6:698-708, 1995.
Christodoulides et al., *Microbiology*, 144(Pt 11):3027-3037, 1998.
Connelly et al., *Endocr. Res.* 30(4):697-703, 2004
Davidson et al., *J. Immunother.*, 21(5):389-398, 1998.
De Paula et al., *RNA*, 13(4):431-56, 2007.
Edelstein et al., *J. Biol. Chem.*, 257:7189-95, 1982.
Egholm et al., *Nature*, 365(6446):566-568, 1993.
Eisenberg, *J. Lipid Res.*, 25:1017-58, 1984.
Elmen et al., *Nucleic Acids Res.*, 33(1):439-447, 2005.
EP 266,032
Fanning et al., *J. Clin. Oncol.*, 9:1668-1674, 1993. Favre et al., 1993)
Feenstra et al., *J. Natl. Cancer Inst.*, 89:582-584, 1997.
Fire et al., *Nature*, 391(6669):806-811, 1998.
Froehler et al., *Nucleic Acids Res.*, 14(13):5399-5407, 1986.
Hanibuchi et al., *Int. J. Cancer*, 78(4):480-485, 1998.
Hellstrand et al., *Acta Oncologica*, 37(4):347-353, 1998.
Hui and Hashimoto, *Infection Immun.*, 66(11):5329-5336, 1998.
Jonas, *Biochim. Biophys. Acia.*, 1084:205-20, 1991.
Ju et al., *Gene Ther.*, 7(19):1672-1679, 2000.
Kawakami and Hashida, *Drug Metab Pharmacokinet.*, 22(3): 142-51, 2007.
Kornberg and Baker, *DNA Replication*, $2^{nd}$ Ed., Freeman, San Francisco, 1992.
Kumar and Clarke, *Adv. Drug Deliv. Rev.*, 59(2-3):87-100, 2007.
Lacko and Chen, *Chromatog.*, 130:446-450, 1977.
Lacko et al., *Anticancer Res.*, 22:2045, 2002.
Lacko et al., *Nanotechnology for Cancer Therapeutics.*, pp 777-785, M. Amiji Editor, CRC Press, 2006.
McConathy et al., *Anti-Cancer Drugs* 19(2):183-188, 2008.
Landen et al., *Cancer Res.*, 65:6910-6918, 2005.
Leung and Whittaker, *Pharmacol. Ther.*, 107(2):222-239, 2005.
Lundberg, *J. Pharm. Pharmacol.*, 49:16-21, 1997.
Massey et al., *Biochem. Biophys. Res. Comm.*, 99:466-74, 1981.
McConathy et al., Anticancer Drugs, 19(2):183-188, 2008.
McGuir et al., *Sem. Oncol.*, 25:340-348, 1998.
McGuire et al., *N. Engl. J. Med.*, 334:1-6, 1996.
Mitchell et al., *Ann. NY Acad. Sci.*, 690:153-166, 1993.
Mitchell et al., *J. Clin. Oncol.*, 8(5):856-869, 1990.
Morton et al., *Arch. Surg.*, 127:392-399, 1992.
Navab et al., *Arterioscler Thromb Vase Biol.* 25:1325-31, 2005.
Navab et al., *Natl. Clin. Pract. Cardiovasc. Med.;* 3:540-7, 2006.
PCT Appln. PCT/EP/01219
PCT Appln. WO 92/20702
Pietras et al., *Oncogene*, 17(17):2235-2249, 1998.
Qin et al., *Proc. Natl. Acad. Sci. USA*, 95(24):14411-14416, 1998.
Ravindranath and Morton, *Intern. Rev. Immunol.*, 7:303-329, 1991.
Rosenberg et al., *Ann. Surg.* 210(4):474-548, 1989.
Rosenberg et al., *N. Engl. J. Med.*, 319:1676, 1988.
Ryan et al., *Protein Expression and Purification*, 27:98-103, 2003.
Saito et al. *Prog. Lipid Res.* 43:350-80, 2004.

Sambrook et al., *In: Molecular cloning*, Cold Spring Harbor Laboratory Press, Cold Spring Harbor, N.Y., 2001.
Sodhi et al., *J. Biol. Chem.*, 242:1205-10, 1967.
Soutschek et al., *Nature*, 432:173-178, 2004.
Tari et al., *Blood*, 84:601-607, 1994.
Thaker et al., *Clin Cancer Res*, 11:4923-4933, 2005.
Vingerhoeds et al., *Br. J. Cancer*, 74:1023-1029, 1996.
Wadhwa et al., *Curr. Opin. Mol. Ther.*, 6(4):367-372, 2004.
Wang et al., *Chem. Pharm. Bull.* (*Tokyo*), 44:1936-1940, 1996.
Weiner, *Immunomethods* 4:201-209, 1994.
Xie et al., *World J Gastroenterol.*, 12(46):7472-7, 2006.

The invention claimed is:

1. A high density lipoprotein-nucleic acid particle comprising:
   a) an apolipoprotein;
   b) a nucleic acid component comprising a therapeutic nucleic acid segment; and
   c) a polypeptide of 2 to 500 consecutive amino acids, wherein the polypeptide comprises a positively-charged region associated with the nucleic acid component;
   wherein the particle comprises a neutral phospholipid, and the neutral phospholipid is 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl- sn-glycero-3-phosphocholine ("DEPC"), palmitoyloleoyl phosphatidylcholine ("POPC"), lyso-phosphatidylcholine, dilinoleoylphosphatidylcholine, distearoylphosphatidylethanolamine ("DSPE"), dimyristoyl phosphatidylethanolamine ("DMPE"), dipalmitoyl phosphatidylethanolamine ("DPPE"), palmitoyloleoyl phosphatidylethanolamine ("POPE"), or lysophosphatidylethanolamine.

2. A high density lipoprotein-nucleic acid particle comprising:
   a) an apolipoprotein;
   b) a nucleic acid component comprising a therapeutic nucleic acid segment; and
   c) a polypeptide of 2 to 500 consecutive amino acids, wherein the polypeptide comprises a positively-charged region associated with the nucleic acid component;
   wherein the particle has a molecular weight of between about 10,000 Daltons to about 1,000,000 Daltons.

3. The high density lipoprotein-nucleic acid particle of claim 2, wherein the apolipoprotein is apolipoprotein AI.

4. The high density lipoprotein-nucleic acid particle of claim 2, wherein the positively-charged region of the polypeptide comprises 2 to 500 consecutive positively-charged amino acid residues.

5. The high density lipoprotein-nucleic acid particle of claim 4, wherein the positively-charged amino acid residues are lysine residues.

6. The high density lipoprotein-nucleic acid particle of claim 5, wherein the positively-charged region of the polypeptide comprises 2 to 40 consecutive lysine residues.

7. The high density lipoprotein-nucleic acid particle of claim 2, further comprising a neutral phospholipid.

8. The high density lipoprotein-nucleic acid particle of claim 2, further comprising cholesteryl oleate.

9. The high density lipoprotein-nucleic acid particle of claim 2, wherein the particle has a molecular size of from about 100 Angstroms to about 300 Angstroms.

10. The high density lipoprotein-nucleic acid particle of claim 2, wherein the particle has a molecular weight of between about 50,000 Daltons to about 500,000 Daltons.

11. The high density lipoprotein-nucleic acid particle of claim 10, wherein the particle has a molecular weight of between about 100,000 Daltons to about 300,000 Daltons.

12. The high density lipoprotein-nucleic acid particle of claim 2, wherein the nucleic acid component comprises a siRNA that downregulates focal adhesion kinase (FAK) expression.

13. The high density lipoprotein-nucleic acid particle of claim 2, wherein the nucleic acid component comprises a siRNA that downregulates STAT3 expression.

14. The high density lipoprotein-nucleic acid particle of claim 2, the particle further comprising a targeting ligand attached to the apolipoprotein.

15. The high density lipoprotein-nucleic acid particle of claim 14, wherein the targeting ligand is a small molecule, a peptide, a polypeptide, a protein, an antibody, or an antibody fragment.

16. A pharmaceutical composition, comprising a high density lipoprotein-nucleic acid particle as set forth in claim 2 and a pharmaceutically acceptable carrier.

17. The pharmaceutical composition of claim 16, the particle further comprising one or more therapeutic agents.

18. The pharmaceutical composition of claim 17, wherein the one or more therapeutic agents are chemotherapeutic agents.

19. A method of treating a subject with a disease comprising administering to the subject a pharmaceutically effective amount of high density lipoprotein-nucleic acid particles as set forth in claim 2.

20. A method of delivering a nucleic acid segment into a cell, comprising contacting the cell with an effective amount of high density lipoprotein-nucleic acid particles as set forth in claim 2.

21. A method of improving the therapeutic efficacy of a chemotherapeutic agent in a subject with cancer, comprising:
   a) administering to a subject with cancer a pharmaceutically effective amount of high density lipoprotein-nucleic acid particles as set forth in claim 2; and
   b) administering a chemotherapeutic agent to the subject, wherein efficacy of the chemotherapeutic agent is improved.

22. A method of reducing the risk of metastasis in a subject with cancer, comprising:
   a) administering to a subject with cancer a pharmaceutically effective amount of high density lipoprotein-nucleic acid particles as set forth in claim 2; and
   b) administering a chemotherapeutic agent to the subject, wherein the risk of metastasis in the subject is reduced.

23. A high density lipoprotein-nucleic acid particle comprising:
  a) an apolipoprotein;
  b) a nucleic acid component comprising a therapeutic nucleic acid segment; and
  c) a polypeptide of 2 to 500 consecutive amino acids, wherein the polypeptide comprises a positively-charged region associated with the nucleic acid component;
  wherein the nucleic acid component comprises a siRNA or shRNA or a nucleic acid encoding a siRNA or shRNA, further wherein in the case of siRNA, the siRNA is a double stranded nucleic acid of 18 to 100 nucleobases.

24. The high density lipoprotein-nucleic acid particle of claim 23, wherein the siRNA is 18 to 30 nucleobases.

25. The high density lipoprotein-nucleic acid particle of claim 23, wherein the nucleic acid component comprises an shRNA or a nucleic acid encoding an shRNA.

* * * * *